United States Patent
Uchiyama et al.

(10) Patent No.: US 12,215,189 B2
(45) Date of Patent: Feb. 4, 2025

(54) BISPHENOL COMPOSITION AND POLYCARBONATE RESIN

(71) Applicant: MITSUBISHI CHEMICAL CORPORATION, Tokyo (JP)

(72) Inventors: Kei Uchiyama, Tokyo (JP); Masashi Yokogi, Tokyo (JP); Hiroki Shibata, Tokyo (JP); Sora Tomita, Tokyo (JP); Yuichi Yayama, Tokyo (JP); Kenji Tsuruhara, Tokyo (JP); Takayuki Yoshida, Tokyo (JP); Yukie Nakashima, Tokyo (JP); Rie Konishi, Tokyo (JP); Kazuo Hirowatari, Tokyo (JP)

(73) Assignee: MITSUBISHI CHEMICAL CORPORATION, Tokyo (JP)

( * ) Notice: Subject to any disclaimer, the term of this patent is extended or adjusted under 35 U.S.C. 154(b) by 693 days.

(21) Appl. No.: 17/472,905

(22) Filed: Sep. 13, 2021

(65) Prior Publication Data

US 2021/0403641 A1 Dec. 30, 2021

Related U.S. Application Data

(63) Continuation of application No. PCT/JP2020/007746, filed on Feb. 26, 2020.

(30) Foreign Application Priority Data

| Mar. 14, 2019 | (JP) | 2019-047450 |
| Mar. 14, 2019 | (JP) | 2019-047453 |
| Mar. 14, 2019 | (JP) | 2019-047454 |
| Dec. 25, 2019 | (JP) | 2019-234571 |
| Dec. 25, 2019 | (JP) | 2019-234572 |

(51) Int. Cl.
| C08G 64/06 | (2006.01) |
| C07C 37/20 | (2006.01) |
| C07C 37/68 | (2006.01) |
| C07C 39/16 | (2006.01) |
| C08G 64/30 | (2006.01) |
| C08G 64/42 | (2006.01) |

(52) U.S. Cl.
CPC ........... *C08G 64/06* (2013.01); *C07C 37/20* (2013.01); *C07C 37/685* (2013.01); *C07C 39/16* (2013.01); *C08G 64/307* (2013.01); *C08G 64/42* (2013.01)

(58) Field of Classification Search
CPC ........ C08G 64/04; C08G 18/44; C08G 64/06; C08L 69/00
See application file for complete search history.

(56) References Cited

U.S. PATENT DOCUMENTS

| 2003/0028055 A1 | 2/2003 | Nakamura et al. |
| 2020/0190003 A1 | 6/2020 | Uchiyama et al. |
| 2020/0190004 A1 | 6/2020 | Uchiyama et al. |

FOREIGN PATENT DOCUMENTS

| CN | 1345297 A | 4/2002 |
| JP | 51-2797 A | 1/1976 |
| JP | S62-138443 A | 6/1987 |
| JP | 06-32885 A | 2/1994 |
| JP | 08-183852 A | 7/1996 |
| JP | H08-225641 A | 9/1996 |
| JP | 2011105932 A | 6/2011 |
| JP | 2011219636 A | 11/2011 |
| JP | 2013072077 A | 4/2013 |
| JP | 2014040376 A | 3/2014 |
| TW | 201843213 A | 12/2018 |
| WO | WO-2019039520 A1 | 2/2019 |

OTHER PUBLICATIONS

Office Action issues Jun. 6, 2023 in Japanese Patent Application No. 2021-504907 (with English translation), 7 pages.
Extended European Search Report issued Apr. 22, 2022 in Patent Application No. 20770715.9, 8 pages.
Combined Chinese Office Action and Search Report issued Jan. 19, 2023 in Patent Application No. 202080020686.4 (with English translation of the Office Action), 18 pages.
International Search Report issued May 26, 2020 in PCT/JP2020/007746 (with English translation), 9 pages.
Combined Office Action and Search Report issued Mar. 13, 2023 in Taiwanese Patent Application No. 109108285 (with English translation), 17 pages.

(Continued)

*Primary Examiner* — Gregory Listvoyb
(74) *Attorney, Agent, or Firm* — Element IP, PLC

(57) ABSTRACT

A bisphenol composition including 95% or more by mass of a bisphenol, wherein a bisphenol represented by the following general formula (II) in the bisphenol composition constitutes 150 mass ppm or more, and the bisphenol composition has a methanol dissolution color (Hazen color number) of 2 or less,

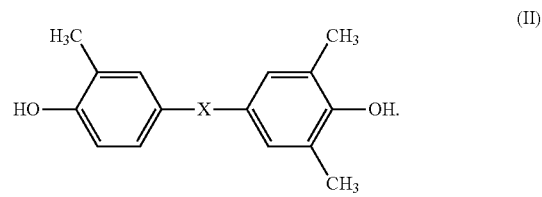

(II)

In formula (II), X denotes a single bond, $-CR^{11}R^{12}-$, $-O-$, $-CO-$, $-S-$, $-SO-$, or $-SO_2-$, $R^{11}$ and $R^{12}$ independently denote a hydrogen atom or an alkyl group having 1 to 10 carbon atoms, and $R^{11}$ and $R^{12}$ may be bonded to each other to form a ring. A method for producing a polycarbonate resin using the bisphenol composition is also described.

15 Claims, No Drawings

(56) References Cited

OTHER PUBLICATIONS

Office Action issued Dec. 9, 2024, in Korean Patent Application No. 10-2021-7029514 (with machine English translation), 25 pages.

BISPHENOL COMPOSITION AND POLYCARBONATE RESIN

TECHNICAL FIELD

The present invention relates to a bisphenol composition, a polycarbonate resin, and a method for producing the bisphenol composition or the polycarbonate resin.

A bisphenol composition according to the present invention is useful as a raw material for a resin, such as a polycarbonate resin, an epoxy resin, or an aromatic polyester resin, a curing agent, a developer, an antifading agent, a bactericide, an antimicrobial and antifungal agent, or another additive agent.

BACKGROUND ART

Bisphenols are useful as raw materials for polymeric materials, such as polycarbonate resins, epoxy resins, and aromatic polyester resins. Examples of known typical bisphenols include 2,2-bis(4-hydroxyphenyl) propane and 2,2-bis(4-hydroxy-3-methylphenyl) propane (Patent Literature 1 and Patent Literature 2).

PTL 1: JP 62-138443A
PTL 2: JP 2014-40376A

Polycarbonate resins, which are typical applications of bisphenols, are required to be colorless and transparent. The color tones of polycarbonate resins are greatly influenced by the color tones of the raw materials. Thus, the color tones of raw material bisphenols are also required to be colorless.

It is difficult to directly quantitatively determine the colors of bisphenols. In the present invention, therefore, a bisphenol is dissolved in methanol to quantify the color difference, and this color tone is referred to as "methanol dissolution color".

In the production of polycarbonate resins, particularly in a melting method, a bisphenol is melted to produce a polycarbonate resin. Thus, the bisphenol is exposed to high temperatures. Bisphenols are therefore also required to have thermally stable color tones.

In the present invention, this color tone is referred to as "molten color".

In the production of polycarbonate resins, a polymerization reaction occurs after a bisphenol is melted. Thus, bisphenols are also required to have thermally stable color tones until the polymerization starts.

In the present invention, this color tone is referred to as "thermal color tone stability".

In the production of polycarbonate resins, if a bisphenol is thermally decomposed before the polymerization starts, the amount of substance of the bisphenol decreases, and the amount of substance ratio of the bisphenol to a raw material diphenyl carbonate deviates from a predetermined amount of substance ratio. Thus, a polycarbonate resin with a desired molecular weight cannot be produced. Bisphenols are therefore also required to be thermally stable.

In the present invention, this stability is referred to as "thermal decomposition stability".

As for polycarbonate resins, there is a demand for a polycarbonate resin with a designed molecular weight and a good color tone. To produce such a polycarbonate resin, there is a demand for a raw material bisphenol with a good methanol dissolution color, a small molten color, high thermal color tone stability, and high thermal decomposition stability.

SUMMARY OF INVENTION

It is an object of the present invention to provide a bisphenol composition with a good methanol dissolution color, a small molten color, high thermal color tone stability, and high thermal decomposition stability. It is another object of the present invention to provide a polycarbonate resin with a good color tone using the bisphenol composition.

The present inventors have found that a bisphenol C composition containing a specific compound at a predetermined ratio has a good methanol dissolution color, a small molten color, high thermal color tone stability, and high thermal decomposition stability. The present inventors have also found that a polycarbonate resin having a structural unit derived from this specific compound at a predetermined ratio has a good color tone.

The gist of a first aspect of the present invention consists in the following [1] to [14].

[1] A bisphenol composition comprising 95% or more by mass of a bisphenol,
wherein a bisphenol represented by the following general formula (II) in the bisphenol composition constitutes 150 mass ppm or more, and
the bisphenol composition has a methanol dissolution color (Hazen color number) of 2 or less,

[Chem. 1]

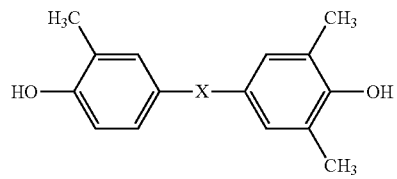

(II)

wherein X denotes a single bond, —CR$^{11}$R$^{12}$—, —O—, —CO—, —S—, —SO—, or —SO$_2$—, R$^{11}$ and R$^{12}$ independently denote a hydrogen atom or an alkyl group having 1 to 10 carbon atoms, and R$^{11}$ and R$^{12}$ may be bonded to each other to form a ring.

[2] The bisphenol composition according to [1], wherein the bisphenol is a bisphenol represented by the following general formula (I),

[Chem. 2]

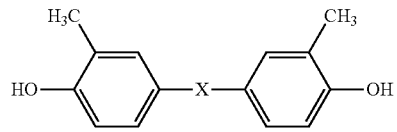

(I)

wherein X denotes a single bond, —CR$^{11}$R$^{12}$—, —O—, —CO—, —S—, —SO—, or —SO$_2$—, R$^{11}$ and R$^{12}$ independently denote a hydrogen atom or an alkyl group having 1 to 10 carbon atoms, and R$^{11}$ and R$^{12}$ may be bonded to each other to form a ring.

[3] The bisphenol composition according to [1] or [2], wherein the bisphenol represented by the general formula (II) in the bisphenol composition constitutes 20,000 mass ppm or less.

[4] The bisphenol composition according to any one of [1] to [3], wherein the bisphenol represented by the general formula (II) is one or more selected from the group consisting of 2-(4-hydroxy-3-methylphenyl)-2-(4-hydroxy-3,5-dimethylphenyl) propane, 1-(4-hydroxy-3-methylphenyl)-1-(4-hydroxy-3,5-dimethylphenyl) cyclohexane, and 1-(4- hydroxy-3-methylphenyl)-1-(4-hydroxy-3,5-dimethylphenyl)-3,3,5-trimethylcyclohexane.

[5] The bisphenol composition according to any one of [1] to [4], wherein the bisphenol composition melted at 190° C. for 30 minutes has a Hazen color number of 100 or less measured with "SE6000" manufactured by Nippon Denshoku Industries Co., Ltd.

[6] The bisphenol composition according to any one of [1] to [5], wherein the bisphenol composition has a sodium content of less than 0.5 mass ppm.

[7] The bisphenol composition according to any one of [1] to [6], wherein the bisphenol composition has an iron content of 0.5 mass ppm or less.

[8] The bisphenol composition according to any one of [1] to [7], wherein the bisphenol composition has an aluminum content of 0.1 mass ppm or less.

[9] The bisphenol composition according to any one of [1] to [8], wherein the bisphenol represented by the general formula (I) is one or more selected from the group consisting of 2,2-bis(4-hydroxy-3-methylphenyl) propane, 1,1-bis(4-hydroxy-3-methylphenyl) cyclohexane, and 1,1-bis(4-hydroxy-3-methylphenyl)-3,3,5-trimethylcyclohexane.

[10] The method for producing a bisphenol composition according to any one of [1] to [9], wherein the bisphenol represented by the general formula (II) is produced as a by-product when the bisphenol is produced.

[11] A method for producing a polycarbonate resin using the bisphenol composition according to any one of [1] to [9].

[12] A polycarbonate resin comprising at least a repeating structural unit represented by the following general formula (A), wherein a compound produced by alkaline hydrolysis of the polycarnate resin contains a bisphenol represented by the following general formula (I) and a bisphenol represented by the following general formula (II), and the bisphenol represented by the following general formula (II) produced by the alkaline hydrolysis constitutes 160 mass ppm or more of the polycarbonate resin,

[Chem. 3]

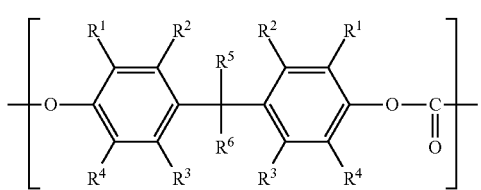

(A)

wherein $R^1$ to $R^6$ independently denote a hydrogen atom, a halogen atom, an alkyl group, an alkoxy group, or an aryl group, and the alkyl group, the alkoxy group, and the aryl group may be substituted or unsubstituted, $R^5$ and $R^6$ may be bonded or cross-linked between the two groups, and $R^5$, $R^6$, and an adjacent carbon atom may be bonded together and form a cycloalkylidene group optionally containing a heteroatom,

[Chem. 4]

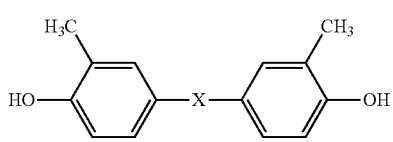

(I)

wherein X denotes a single bond, $-CR^{11}R^{12}-$, $-O-$, $-CO-$, $-S-$, $-SO-$, or $-SO_2-$, $R^{11}$ and $R^{12}$ independently denote a hydrogen atom or an alkyl group having 1 to 10 carbon atoms, and $R^{11}$ and $R^{12}$ may be bonded to each other to form a ring,

[Chem. 5]

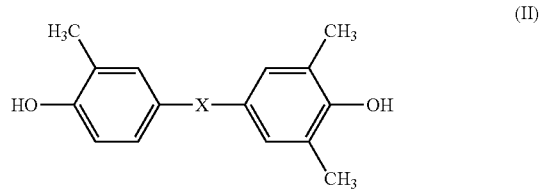

(II)

wherein X denotes a single bond, $-CR^{11}R^{12}-$, $-O-$, $-CO-$, $-S-$, $-SO-$, or $-SO_2-$, $R^{11}$ and $R^{12}$ independently denote a hydrogen atom or an alkyl group having 1 to 10 carbon atoms, and $R^{11}$ and $R^{12}$ may be bonded to each other to form a ring.

[13] The polycarbonate resin according to [12], wherein the bisphenol represented by the general formula (II) constitutes 20,000 mass ppm or less of the polycarbonate resin.

[14] The polycarbonate resin according to [12] or [13], wherein the polycarbonate resin has a viscosity-average molecular weight of 15,000 or more and 35,000 or less.

Advantageous Effects of Invention

The present invention provides a bisphenol composition containing a specific compound at a predetermined ratio with a good methanol dissolution color, a small molten color, high thermal color tone stability, and high thermal decomposition stability.

The present invention provides, as a polycarbonate resin with a good color tone, a polycarbonate resin produced from the bisphenol composition, that is, a polycarbonate resin in which the specific compound is produced by alkaline hydrolysis at a predetermined ratio.

DESCRIPTION OF EMBODIMENTS

Embodiments of the present invention are described in detail below. The following description of the constituent features is an example of embodiments of the present invention, and the present invention is not limited to the following description as long as it does not depart from the gist thereof.

In the expression "to" in the present specification, the expression includes numerical values or physical properties before and after the expression.

[Bisphenol Composition]

A bisphenol composition according to the present invention is characterized by containing 95% or more by mass of a bisphenol, wherein a bisphenol represented by the following general formula (II) in the bisphenol composition constitutes 150 mass ppm or more, and the bisphenol composition has a methanol dissolution color (Hazen color number) of 2 or less,

[Chem. 6]

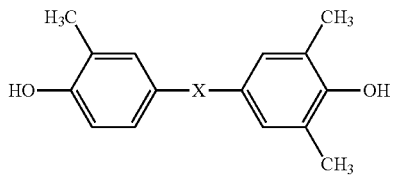

(II)

wherein X denotes a single bond, —CR$^{11}$R$^{12}$—, —O—, —CO—, —S—, —SO—, or —SO$_2$—, R$^{11}$ and R$^{12}$ independently denote a hydrogen atom or an alkyl group having 1 to 10 carbon atoms, and R$^{11}$ and R$^{12}$ may be bonded to each other to form a ring.

A bisphenol composition according to the present invention preferably has a bisphenol (II) content of 200 mass ppm or more, more preferably 250 mass ppm or more, particularly preferably 300 mass ppm or more, and preferably 20,000 mass ppm or less, more preferably 15,000 mass ppm or less, still more preferably 1400 mass ppm or less, particularly preferably 1300 mass ppm or less.

When the bisphenol (II) content of the bisphenol composition is below the lower limit, it is impossible to produce a bisphenol composition with a good methanol dissolution color, a small molten color, high thermal color tone stability, and high thermal decomposition stability. A bisphenol (II) content of the bisphenol composition above the upper limit results in the following tendencies.

1) When a polycarbonate resin is produced, the mole ratio with respect to diphenyl carbonate deviates, and the polymerization reaction is affected.

2) The brittleness (Izod) of a polycarbonate resin produced from the bisphenol composition decreases, and the high surface hardness characteristic of a polycarbonate resin with a structural unit derived from a bisphenol (I) described later decreases.

More specifically, the bisphenol (II) may be one or more selected from the group consisting of 2-(4-hydroxy-3-methylphenyl)-2-(4-hydroxy-3,5-dimethylphenyl) propane, 1-(4-hydroxy-3-methylphenyl)-1-(4-hydroxy-3,5-dimethylphenyl) cyclohexane, and 1-(4-hydroxy-3-methylphenyl)-1-(4-hydroxy-3,5-dimethylphenyl)-3,3,5-trimethylcyclohexane. Among these, 2-(4-hydroxy-3-methylphenyl)-2-(4-hydroxy-3,5-dimethylphenyl) propane (hereinafter referred to as a "trimethyl bisphenol A") is particularly preferred.

The bisphenol (II) can be detected and quantitatively determined with a standard high-speed analytical reversed-phase column with a particle size of 3 μm.

The bisphenol (II) content of the bisphenol composition can be adjusted by adding an appropriate amount of the bisphenol (II) to a bisphenol containing no purified bisphenol (II) or containing a low concentration of a purified bisphenol (II). Furthermore, as described later, a bisphenol product containing the bisphenol (II) can be prepared as a bisphenol composition according to the present invention by producing the bisphenol (II) together with the bisphenol in the reaction system when the bisphenol is produced.

<Bisphenol>

A bisphenol in a bisphenol composition according to the present invention is typically a compound represented by the following general formula (1).

[Chem. 7]

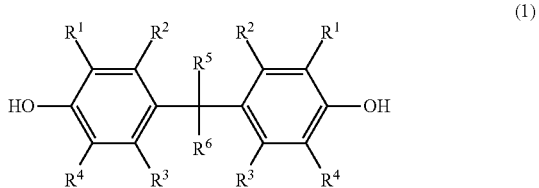

(1)

In the general formula (1), R$^1$ to R$^6$ have the same meaning as R$^1$ to R$^6$ in the general formulae (3) and (4) described later, and preferred examples and specific examples thereof are as described for the general formulae (3) and (4).

Specific examples of the bisphenol represented by the general formula (1) include, but are not limited to, 2,2-bis(4-hydroxyphenyl) propane, 2,2-bis(4-hydroxy-3-methylphenyl) propane, 2,2-bis(4-hydroxy-3,5-dimethylphenyl) propane, 1,1-bis(4-hydroxy-3-methylphenyl) cyclohexane, 1,1-bis(4-hydroxy-3-methylphenyl)-3,3,5-trimethylcyclohexane, 9,9-bis(4-hydroxy-3-methylphenyl) fluorene, 3,3-bis(4-hydroxyphenyl) pentane, 3,3-bis(4-hydroxy-3-methylphenyl) pentane, 2,2-bis(4-hydroxyphenyl) pentane, 2,2-bis(4-hydroxy-3-methylphenyl) pentane, 3,3-bis(4-hydroxyphenyl) heptane, 3,3-bis(4-hydroxy-3-methylphenyl) heptane, 2,2-bis(4-hydroxyphenyl) heptane, 2,2-bis(4-hydroxy-3-methylphenyl) heptane, 4,4-bis(4-hydroxyphenyl) heptane, and 4,4-bis(4-hydroxy-3-methylphenyl) heptane.

Among these, as a bisphenol in a bisphenol composition according to the present invention, a bisphenol represented by the following general formula (I) (hereinafter also referred to as a "bisphenol (I)") is preferred. The bisphenol (I) is preferably one or more selected from the group consisting of 2,2-bis(4-hydroxy-3-methylphenyl) propane, 1,1-bis(4-hydroxy-3-methylphenyl) cyclohexane, and 1,1-bis(4-hydroxy-3-methylphenyl)-3,3,5-trimethylcyclohexane. In particular, 2,2-bis(4-hydroxy-3-methylphenyl) propane (bisphenol C) is preferred.

[Chem. 8]

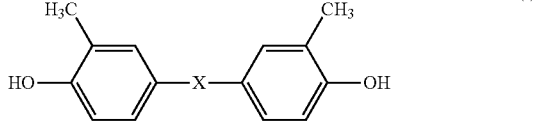

(I)

wherein X denotes a single bond, —CR$^{11}$R$^{12}$—, —O—, —CO—, —S—, —SO—, or —SO$_2$—, R$^{11}$ and R$^{12}$ independently denote a hydrogen atom or an alkyl group having 1 to 10 carbon atoms, and R$^{11}$ and R$^{12}$ may be bonded to each other to form a ring.

The bisphenol composition according to the present invention contains 95% or more by mass, preferably 99% or more by mass, still more preferably 99.5% or more by mass, of such a bisphenol. A bisphenol content below the lower limit is undesirable for use as a bisphenol. The upper limit of the bisphenol content of the bisphenol composition according to the present invention is typically approximately 99.9% by mass in terms of the bisphenol (II) content, production costs, the adjustment of the amount of substance ratio of bisphenol to diphenyl carbonate in the production reaction of a polycarbonate resin, and the mechanical properties of the polycarbonate resin, such as surface hardness and brittleness.

Bisphenols can be detected and quantitatively determined with a standard high-speed analytical reversed-phase column.

<Methanol Dissolution Color of Bisphenol Composition>

The methanol dissolution color of a bisphenol composition is used to evaluate the color tone of the bisphenol composition at normal temperature. A bisphenol composition with a lower Hazen color number of the methanol dissolution color has a better color tone (closer to white). A poor methanol dissolution color of a bisphenol composition may be caused by contamination with an organic coloring component or a metal.

The methanol dissolution color of a bisphenol composition is measured at room temperature (approximately 20° C.) after the bisphenol composition is dissolved in methanol to prepare a homogeneous solution. Examples of the measurement method include a method of visual comparison with a standard liquid of the Hazen color number or a method of measuring the Hazen color number with a color difference meter, such as "SE6000" manufactured by Nippon Denshoku Industries Co., Ltd. The solvent methanol and the mass ratio of bisphenol to the solvent are preferably appropriately selected in accordance with the type of bisphenol.

The Hazen color number of the methanol dissolution color of the bisphenol composition according to the present invention is 2 or less, preferably 1 or less, more preferably 0 or less.

<Molten color of Bisphenol Composition>

The molten color of a bisphenol composition is used to evaluate the color tone of the bisphenol composition at a temperature close to the polymerization temperature of the polycarbonate. The molten color is measured at the melting point of the bisphenol+50° C. With respect to the molten color, a bisphenol composition with a lower Hazen color number has a better color tone (closer to white). An increase in the molten color of a bisphenol composition may be caused by a component that is colored by heating as well as contamination with an organic coloring component or a metal.

The molten color of a bisphenol composition is measured by melting the bisphenol composition at a temperature close to the polymerization temperature and performing the measurement when the temperature is stabilized in advance. Examples of the measurement method include a method of visual comparison with a standard liquid of the Hazen color number or a method of measuring the Hazen color number with a color difference meter, such as "SE6000" manufactured by Nippon Denshoku Industries Co., Ltd.

A bisphenol composition according to the present invention melted at 190° C. for 30 minutes preferably has a Hazen color number of 100 or less, more preferably 30 or less, particularly preferably 25 or less, particularly preferably 20 or less, measured with "SE6000" manufactured by Nippon Denshoku Industries Co., Ltd.

<Thermal Color Tone Stability of Bisphenol Composition>

Like the molten color of a bisphenol composition, the thermal color tone stability of a bisphenol composition is used to evaluate the thermal stability of the color tone of the bisphenol composition by holding the bisphenol composition for a predetermined time at a temperature close to the polymerization temperature of the polycarbonate. The thermal color tone stability of a bisphenol composition is measured at the melting point of the bisphenol+50° C.

A bisphenol composition with a lower Hazen color number has higher thermal color tone stability. A decrease in the thermal color tone stability of a bisphenol composition may be caused by a component that is colored by heating or an acidic or basic substance with a concentration of several ppm as well as contamination with an organic coloring component or a metal.

The thermal color tone stability of a bisphenol composition is measured by melting the bisphenol composition at a temperature close to the polymerization temperature and performing the measurement when the temperature is stabilized in advance. The holding time for the thermal color tone stability of the bisphenol composition is 4 hours. Examples of the measurement method include a method of visual comparison with a standard liquid of the Hazen color number or a method of measuring the Hazen color number with a color difference meter, such as "SE6000" manufactured by Nippon Denshoku Industries Co., Ltd.

The Hazen color number is preferably 50 or less, more preferably 45 or less, particularly preferably 35 or less.

<Thermal Decomposition Stability of Bisphenol Composition>

Like the thermal color tone stability of a bisphenol composition, the thermal decomposition stability of a bisphenol composition is used to evaluate the thermal stability of the bisphenol composition by holding the bisphenol composition for a predetermined time at a temperature close to the polymerization temperature of the polycarbonate. The thermal decomposition stability of a bisphenol composition is preferably measured at the melting point of the bisphenol+50° C. With respect to the thermal decomposition stability of a bisphenol composition, a smaller amount of decomposition product indicates a more stable bisphenol composition.

The decomposition product in the thermal decomposition stability of a bisphenol composition may be an aromatic alcohol that is a raw material of the bisphenol composition or an addition product of the aromatic alcohol and a raw material ketone or aldehyde, depending on the type of bisphenol. A decrease in the thermal decomposition stability of a bisphenol composition may be caused by a component that is colored by heating or an acidic or basic substance with a concentration of several ppm as well as contamination with an organic coloring component or a metal. Decomposition products of a bisphenol composition can be detected and quantitatively determined with a standard high-speed analytical reversed-phase column.

The amount of isopropenyl cresol produced as a decomposition product of the bisphenol composition measured in the examples described later is preferably 200 mass ppm or less.

The methanol dissolution color of a bisphenol composition is a measure of the color tone of the bisphenol composition itself. When a bisphenol composition is a final product, a bisphenol composition with a good methanol dissolution color is important. Polycarbonate resins have a color tone originating from their raw materials. Thus, a bisphenol composition with a good color tone is important for a colorless and transparent polycarbonate resin.

In a melt polymerization method, which is a method for producing a polycarbonate resin, a polymerization reaction is performed at a high temperature. Thus, the important items are the color tone of a molten bisphenol composition (the molten color of the bisphenol composition) and the color tone stability of the bisphenol composition in the molten state (the thermal color tone stability of the bisphenol composition).

In the melt polymerization method, a bisphenol composition is held in the molten state at a high temperature until the polymerization reaction starts. In the melt polymerization method, when a bisphenol composition decomposes at a high temperature, the amount of substance ratio with respect to diphenyl carbonate deviates from a predetermined amount of substance ratio, and it becomes difficult to produce a polycarbonate resin with polymerization reaction activity and a predetermined molecular weight. Thus, resistance to thermal decomposition (the thermal decomposition stability of a bisphenol composition) is important.

In particular, to produce a polycarbonate resin with a predetermined molecular weight and good color tone, the important items are the methanol dissolution color of a bisphenol composition, the molten color of the bisphenol composition, the thermal color tone stability of the bisphenol composition, and the thermal decomposition stability of the bisphenol composition.

<Sodium Content of Bisphenol Composition>

A bisphenol composition according to the present invention preferably has a sodium content of less than 0.5 mass ppm, more preferably less than 0.4 mass ppm, particularly preferably less than 0.3 mass ppm. Sodium in the bisphenol composition has a catalytic action, and therefore a high sodium content results in a decrease in thermal color tone stability and thermal decomposition stability. Thus, a bisphenol composition according to the present invention preferably has a sodium content equal to or lower than the upper limit.

The sodium content of the bisphenol composition is determined by a method described below in the examples.

<Iron Content of Bisphenol Composition>

The bisphenol composition according to the present invention preferably has an iron content of 0.5 mass ppm or less, more preferably 0.4 mass ppm or less, particularly preferably 0.3 mass ppm or less. Iron in the bisphenol composition has a structure in which the bisphenol coordinates and therefore has absorption in the visible region. Thus, the iron is a coloring factor of the bisphenol composition, and a high iron content results in a poor methanol dissolution color and an increased molten color. The iron has a catalytic action, and therefore a high iron content results in a decrease in thermal color tone stability and thermal decomposition stability. Thus, the bisphenol composition according to the present invention preferably has an iron content equal to or lower than the upper limit.

The iron in the bisphenol composition according to the present invention may be iron dissolved in an aromatic alcohol that is a bisphenol raw material or iron incorporated from a reaction vessel or equipment on top of the reaction vessel during a bisphenol producing reaction. Depending on the form of iron, the iron may be appropriately removed by a purification method described later, such as by repeating washing with water under acidic conditions or by repeating washing with water under basic conditions.

The iron content of the bisphenol composition is determined by a method described below in the examples.

<Aluminum Content of Bisphenol Composition>

The bisphenol composition according to the present invention preferably has an aluminum content of 0.1 mass ppm or less, more preferably 0.09 mass ppm or less, particularly preferably 0.08 mass ppm or less. Aluminum in the bisphenol composition has a structure in which the bisphenol coordinates and therefore has absorption in the visible region. Thus, the aluminum is a coloring factor of the bisphenol composition, and a high iron content results in a poor methanol dissolution color and an increased molten color. The aluminum has a catalytic action, and therefore a high iron content results in a decrease in thermal color tone stability and thermal decomposition stability. Thus, the bisphenol composition according to the present invention preferably has an aluminum content equal to or lower than the upper limit.

The aluminum in the bisphenol composition according to the present invention may be aluminum dissolved in an aromatic alcohol that is a bisphenol raw material or aluminum derived from aluminum oxide incorporated from the outside when a solid bisphenol is taken out or is supplied to a dryer. Depending on the form of aluminum, the aluminum may be appropriately removed by a purification method described later, such as by repeating washing with water under acidic conditions or by repeating washing with water under basic conditions.

The aluminum content of the bisphenol composition is determined by a method described below in the examples.

<Method for Producing Bisphenol Composition>

A method for producing a bisphenol composition according to the present invention that contains 95% or more by mass of a bisphenol, preferably the bisphenol (I), and a predetermined percentage of the bisphenol (II) is, but not limited to, one of the following methods, for example.

(1) A method of adding a predetermined amount of bisphenol (II) to a solid bisphenol (I).

(2) A method of adding a predetermined amount of bisphenol (II) to a molten bisphenol (I).

(3) A method of producing the bisphenol (II) as a by-product or producing the bisphenol (II) together with the bisphenol (I) in the production of the bisphenol (I) to produce a bisphenol (I) product containing the bisphenol (II).

In the method (1) or (2) of adding the bisphenol (II) to the solid or molten bisphenol (I), the bisphenol (II) must be separately prepared. Thus, the method (3) of producing the bisphenol (II) as a by-product or producing the bisphenol (II) in the reaction system for producing the bisphenol (I) to produce a bisphenol (I) product containing a predetermined percentage of the bisphenol (II) is preferred.

When an excessive amount of bisphenol (II) is produced as a by-product or produced in the bisphenol (I) reaction system, the bisphenol (I) product can be further purified by crystallization, suspension washing, or sprinkling washing to remove part of the bisphenol (II) from the bisphenol (I) product and produce the bisphenol (I) product containing the bisphenol (II) within the specified range of the present invention.

<Method for Producing Bisphenol C Product Containing Bisphenol (II)>

Now, a method for producing a bisphenol composition according to the present invention containing a predetermined amount of bisphenol (II) and composed mainly of the bisphenol (I) is described by a typical example in which the bisphenol (II) is a trimethyl bisphenol A and the bisphenol (I) is the bisphenol C.

A method for producing a bisphenol C product containing a trimethyl bisphenol A as a bisphenol composition according to the present invention by producing the trimethyl bisphenol A together with the bisphenol C in the reaction system when the bisphenol C is produced may be a method for producing the bisphenol C or the trimethyl bisphenol A together with the bisphenol C by condensing a ketone or aldehyde and an aromatic alcohol in the presence of an acid catalyst and a thiol promoter. This method can produce a trimethyl bisphenol A in the reaction system.

This method is described below.

In this method, the bisphenol C is produced by condensing the aromatic alcohol and the ketone or aldehyde in the presence of the acid catalyst.

The bisphenol producing reaction is performed in accordance with the following reaction general formula (2). In the present invention, a raw material aromatic alcohol and a raw material ketone or aldehyde are selected and used such that at least the bisphenol C is produced in such a bisphenol producing reaction.

[Chem. 9]

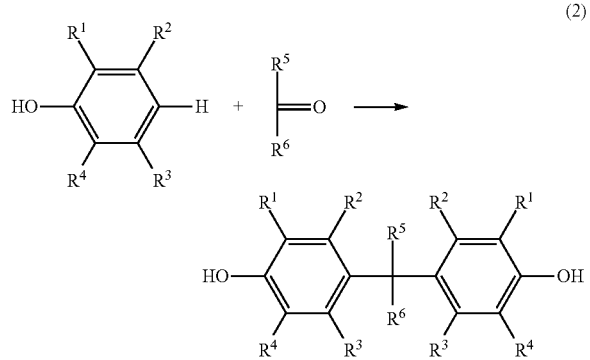

(2)

In the formula, $R^1$ to $R^6$ have the same meaning as in the general formula (1).

(Aromatic Alcohol)

The raw material aromatic alcohol used for the production of the bisphenol is typically a compound represented by the following general formula (3).

[Chem. 10]

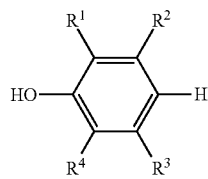

(3)

In the general formula (3), $R^1$ to $R^4$ independently denote a hydrogen atom, a halogen atom, an alkyl group, an alkoxy group, an aryl group, or the like. The alkyl group, the alkoxy group, and the aryl group may be substituted or unsubstituted. For example, $R^1$ to $R^4$ denote a hydrogen atom, a fluoro group, a chloro group, a bromo group, an iodo group, a methyl group, an ethyl group, a n-propyl group, an i-propyl group, a n-butyl group, an i-butyl group, a t-butyl group, a n-pentyl group, an i-pentyl group, a n-hexyl group, a n-heptyl group, a n-octyl group, a n-nonyl group, a n-decyl group, a n-undecyl group, a n-dodecyl group, a methoxy group, an ethoxy group, a n-propoxy group, an i-propoxy group, a n-butoxy group, an i-butoxy group, a t-butoxy group, a n-pentyloxy group, an i-pentyloxy group, a n-hexyloxy group, a n-heptyloxy group, a n-octyloxy group, a n-nonyloxy group, a n-decyloxy group, a n-undecyloxy group, a n-dodecyloxy group, a cyclopropyl group, a cyclobutyl group, a cyclopentyl group, a cyclohexyl group, a cycloheptyl group, a cyclooctyl group, a cyclododecyl group, a benzyl group, a phenyl group, a tolyl group, or a 2,6-dimethylphenyl group.

Among these, $R^2$ and $R^3$ preferably denote a hydrogen atom because sterically bulky $R^2$ and $R^3$ slow down the condensation reaction. $R^1$ to $R^4$ more preferably independently denote a hydrogen atom or an alkyl group. Still more preferably, $R^1$ and $R^4$ independently denote a hydrogen atom or an alkyl group, and $R^2$ and $R^3$ denote a hydrogen atom.

More specifically, the compound represented by the general formula (3) may be phenol, cresol, xylenol, ethylphenol, propylphenol, butylphenol, methoxyphenol, ethoxyphenol, propoxyphenol, butoxyphenol, benzylphenol, or phenylphenol.

In the present invention, among these, at least ortho-cresol is used to produce the bisphenol C, or ortho-cresol and xylenol are used to produce the bisphenol C and a trimethyl bisphenol A.

(Ketone or Aldehyde)

The raw material ketone or aldehyde used for the production of the bisphenol is typically a compound represented by the following general formula (4).

[Chem. 11]

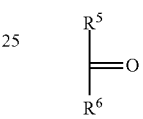

(4)

In the general formula (4), $R^5$ and $R^6$ independently denote a hydrogen atom, an alkyl group, an alkoxy group, an aryl group, or the like. The alkyl group, the alkoxy group, and the aryl group may be substituted or unsubstituted. For example, $R^5$ and $R^6$ denote a hydrogen atom, a methyl group, an ethyl group, a n-propyl group, an i-propyl group, a n-butyl group, an i-butyl group, a t-butyl group, a n-pentyl group, an i-pentyl group, a n-hexyl group, a n-heptyl group, a n-octyl group, a 2-ethylhexyl group, a n-nonyl group, a n-decyl group, a n-undecyl group, a n-dodecyl group, a methoxy group, an ethoxy group, a n-propoxy group, an i-propoxy group, a n-butoxy group, an i-butoxy group, a t-butoxy group, a n-pentyloxy group, an i-pentyloxy group, a n-hexyloxy group, a n-heptyloxy group, a n-octyloxy group, a n-nonyloxy group, a n-decyloxy group, a n-undecyloxy group, a n-dodecyloxy group, a cyclopropyl group, a cyclobutyl group, a cyclopentyl group, a cyclohexyl group, a cycloheptyl group, a cyclooctyl group, a cyclododecyl group, a benzyl group, a phenyl group, a tolyl group, or a 2,6-dimethylphenyl group.

$R^5$ and $R^6$ may be bonded or cross-linked between the two groups. $R^5$, $R^6$, and an adjacent carbon atom may be bonded together and form a cycloalkylidene group optionally containing a heteroatom. The cycloalkylidene group is a divalent group in which two hydrogen atoms are removed from one carbon atom of a cycloalkane.

Examples of the cycloalkylidene group formed by bonding $R^5$, $R^6$, and an adjacent carbon atom include cyclopropylidene, cyclobutylidene, cyclopentylidene, cyclohexylidene, 3,3,5-trimethylcyclohexylidene, cycloheptylidene, cyclooctylidene, cyclononylidene, cyclodecylidene, cycloundecylidene, cyclododecylidene, fluorenylidene, xanthenylidene, and thioxanthenylidene.

More specifically, the compound represented by the general formula (4) may be an aldehyde, such as formaldehyde, acetaldehyde, propionaldehyde, butyl aldehyde, pentyl aldehyde, hexyl aldehyde, heptyl aldehyde, octyl aldehyde, nonyl aldehyde, decyl aldehyde, undecyl aldehyde, or dodecyl aldehyde; a ketone, such as acetone, butanone, pentanone, hexanone, heptanone, octanone, nonanone, decanone, undecanone, or dodecanone; benzaldehyde, an aryl alkyl ketone, such as phenyl methyl ketone, phenyl ethyl ketone, phenyl propyl ketone, cresyl methyl ketone, cresyl ethyl ketone, cresyl propyl ketone, xylyl methyl ketone, xylyl ethyl ketone, or xylyl propyl ketone, or a cyclic alkane ketone, such as cyclopropanone, cyclobutanone, cyclopentanone, cyclohexanone, cycloheptanone, cyclooctanone, cyclononanone, cyclodecanone, cycloundecanone, or cyclododecanone.

In the present invention, at least acetone is used among these.

In the condensation reaction of the aromatic alcohol and the ketone or aldehyde, a low mole ratio of the aromatic alcohol to the ketone or aldehyde results in oligomerization of the ketone or aldehyde, and a high mole ratio of the aromatic alcohol to the ketone or aldehyde results in a loss of unreacted aromatic alcohol. Thus, the mole ratio of the aromatic alcohol to the ketone or aldehyde is preferably 1.5 or more, more preferably 1.6 or more, still more preferably 1.7 or more, and preferably 15 or less, more preferably 10 or less, still more preferably 8 or less.

The ketone or aldehyde may be supplied at a time or two or more times. The bisphenol producing reaction is an exothermic reaction, and therefore the ketone or aldehyde is preferably supplied two or more times, for example, by dropwise addition.

(Acid Catalyst)

The acid catalyst used in the production of the bisphenol may be sulfuric acid, hydrochloric acid, hydrogen chloride gas, phosphoric acid, an aromatic sulfonic acid, such as p-toluenesulfonic acid, or an aliphatic sulfonic acid, such as methanesulfonic acid.

A low mole ratio of the acid catalyst to the ketone or aldehyde used in the condensation ((the number of moles of the acid catalyst/the number of moles of the ketone) or (the number of moles of the acid catalyst/the number of moles of the aldehyde)) results in a long reaction time because the acid catalyst is diluted by water produced as a by-product as the condensation reaction proceeds. A high mole ratio may result in oligomerization of the ketone or aldehyde. Thus, the mole ratio of the acid catalyst to the ketone or aldehyde used in the condensation is preferably 0.01 or more, more preferably 0.05 or more, still more preferably 0.1 or more, and preferably 10 or less, more preferably 8 or less, still more preferably 5 or less.

The acid catalyst is preferably any one selected from the group consisting of sulfuric acid, hydrochloric acid, hydrogen chloride gas, phosphoric acid, aromatic sulfonic acids, such as p-toluenesulfonic acid, and aliphatic sulfonic acids, such as methanesulfonic acid.

A low mole ratio of the hydrogen chloride to the ketone or aldehyde used in the reaction ((the number of moles of the hydrogen chloride/the number of moles of the ketone) or (the number of moles of the hydrogen chloride/the number of moles of the aldehyde)) results in a long reaction time because the hydrogen chloride is diluted by water produced as a by-product in the condensation reaction. A high mole ratio may result in oligomerization of the ketone or aldehyde. Thus, the mole ratio of the hydrogen chloride to the ketone or aldehyde is preferably 0.01 or more, more preferably 0.05 or more, still more preferably 0.1 or more, and preferably 10 or less, more preferably 8 or less, still more preferably 5 or less.

Sulfuric acid is an acidic liquid represented by the chemical formula $H_2SO_4$. Sulfuric acid is typically used as aqueous sulfuric acid diluted with water and is called concentrated sulfuric acid or dilute sulfuric acid depending on its concentration. For example, dilute sulfuric acid is aqueous sulfuric acid with a mass concentration of less than 90% by mass.

A low concentration of sulfuric acid (concentration of aqueous sulfuric acid) used may result in an increased amount of water, a slow bisphenol C producing reaction, a long time of the bisphenol producing reaction, and inefficient production of the bisphenol. Thus, the concentration of sulfuric acid to be used is preferably 70% or more by mass, more preferably 75% or more by mass, still more preferably 80% or more by mass. The upper limit of the concentration of sulfuric acid to be used is typically 99.5% or less by mass or 99% or less by mass.

(Thiol)

In the production of the bisphenol, a thiol can be used as a promoter in the condensation reaction of the ketone or aldehyde and the aromatic alcohol.

The use of a thiol as a promoter, for example, in the production of 2,2-bis(4-hydroxy-3-methylphenyl) propane can suppress the production of a 24 form, increase the selectivity of a 44 form, increase the polymerization activity in the production of the polycarbonate resin, and improve the color tone of the polycarbonate resin.

Although the reason for the improved polymerization activity in the production of the polycarbonate resin and the improved color tone of the polycarbonate resin is not clear in detail, it is assumed that the use of a thiol can suppress the formation of an inhibitor for the polymerization reaction to produce the polycarbonate resin and suppress the formation of a substance that impairs the color tone.

Examples of the thiol used as a promoter include mercaptocarboxylic acids, such as mercaptoacetic acid, thioglycolic acid, 2-mercaptopropionic acid, 3-mercaptopropionic acid, and 4-mercaptobutyric acid, alkyl thiols, such as methyl mercaptan, ethyl mercaptan, propyl mercaptan, butyl mercaptan, pentyl mercaptan, hexyl mercaptan, heptyl mercaptan, octyl mercaptan, nonyl mercaptan, decyl mercaptan (decane thiol), undecyl mercaptan (undecane thiol), dodecyl mercaptan (dodecane thiol), tridecyl mercaptan, tetradecyl mercaptan, and pentadecyl mercaptan, and aryl thiols, such as mercaptophenol.

A low mole ratio of the thiol promoter to the ketone or aldehyde used in the condensation ((the number of moles of the thiol promoter/the number of moles of the ketone) or (the number of moles of the thiol promoter/the number of moles of the aldehyde)) cannot produce the effect of improving the reaction selectivity of the bisphenol due to the use of the thiol promoter. A high mole ratio may result in poor quality due to contamination in the bisphenol. Thus, the mole ratio of the thiol promoter to the ketone or aldehyde is preferably 0.001 or more, more preferably 0.005 or more, still more preferably 0.01 or more, and preferably 1 or less, more preferably 0.5 or less, still more preferably 0.1 or less.

The thiol promoter is preferably mixed with the ketone or aldehyde before the reaction. The thiol and the ketone or aldehyde may be mixed by mixing the thiol with the ketone or aldehyde or mixing the ketone or aldehyde with the thiol.

A liquid mixture of the thiol and the ketone or aldehyde and the acid catalyst may be mixed by mixing the liquid mixture of the thiol and the ketone or aldehyde with the acid catalyst or mixing the acid catalyst with the liquid mixture of the thiol and the ketone or aldehyde, preferably mixing the acid catalyst with the liquid mixture of the thiol and the ketone or aldehyde. More preferably, the acid catalyst and the aromatic alcohol are supplied to a reaction vessel, and then the liquid mixture of the thiol and the ketone or aldehyde is supplied to the reaction vessel and mixed.
(Organic Solvent)

In the production of the bisphenol, an organic solvent is typically used to dissolve or disperse the bisphenol to be produced.

The organic solvent is not particularly limited as long as it does not inhibit the bisphenol C producing reaction and may be an aromatic hydrocarbon, an aliphatic alcohol, or an aliphatic hydrocarbon. The substrate aromatic alcohol and the product bisphenol are excluded from the organic solvent. These solvents may be used alone or in combination.

The aromatic hydrocarbon is benzene, toluene, xylene, ethylbenzene, diethylbenzene, isopropylbenzene, or mesitylene, for example. These solvents may be used alone or in combination. After used for the production of the bisphenol, the aromatic hydrocarbon can be recovered by distillation or the like, purified, and reused. For reuse, the aromatic hydrocarbon preferably has a low boiling point. One of preferred aromatic hydrocarbons is toluene.

The aliphatic alcohol is an alkyl alcohol in which an alkyl group is bonded to a hydroxy group. The aliphatic alcohol may be a monohydric aliphatic alcohol in which an alkyl group is bonded to one hydroxy group or a polyhydric aliphatic alcohol in which an alkyl group is bonded to two or more hydroxy groups. The alkyl group may be linear or branched, may be unsubstituted, or carbon atoms of the alkyl group may be partially substituted with an oxygen atom.

The aliphatic alcohol with an increased number of carbon atoms has increased lipophilicity, is less likely to be miscible with sulfuric acid, and is less likely to produce a monoalkyl sulfate described later. Thus, the number of carbon atoms is preferably 12 or less, more preferably 8 or less.

The aliphatic alcohol is preferably an alcohol in which an alkyl group is bonded to one hydroxy group, more preferably an alcohol in which an alkyl group with 1 to 8 carbon atoms is bonded to one hydroxy group, still more preferably an alcohol in which an alkyl group with 1 to 5 carbon atoms is bonded to one hydroxy group.

More specifically, the aliphatic alcohol is methanol, ethanol, n-propanol, i-propanol, n-butanol, i-butanol, t-butanol, n-pentanol, i-pentanol, n-hexanol, n-heptanol, n-octanol, n-nonanol, n-decanol, n-undecanol, n-dodecanol, ethylene glycol, diethylene glycol, or triethylene glycol, for example. One of preferred aliphatic alcohols is methanol.

The aliphatic hydrocarbon may be a linear hydrocarbon with 5 to 18 carbon atoms, such as n-pentane, n-hexane, n-heptane, or n-octane, a branched hydrocarbon with 5 to 18 carbon atoms, such as isooctane, or a cyclic hydrocarbon with 5 to 18 carbon atoms, such as cyclohexane, cyclooctane, or methylcyclohexane.

An excessively high mass ratio of the organic solvent to the ketone or aldehyde used in the condensation ((the mass of the ketone/the mass of the organic solvent) or (the mass of the aldehyde/the mass of the organic solvent)) results in a slow reaction between the ketone or aldehyde and the aromatic alcohol and a long reaction time. An excessively low mass ratio may result in promoted oligomerization of the ketone or aldehyde and solidification of the bisphenol produced. Thus, the mass ratio of the organic solvent to the ketone or aldehyde at the time of charging is preferably 0.5 or more, more preferably 1 or more, and preferably 100 or less, more preferably 50 or less.

The resulting bisphenol is less likely to decompose when the bisphenol is dispersed rather than completely dissolved in the organic solvent. The solvent also preferably has low bisphenol solubility to decrease the recovery loss of bisphenol from the reaction liquid (for example, a loss as a filtrate during crystallization) after completion of the reaction. The solvent with low bisphenol solubility is an aromatic hydrocarbon, for example. Thus, the organic solvent preferably contains an aromatic hydrocarbon as a main component, preferably 55% or more by mass of an aromatic hydrocarbon, more preferably 70% or more by mass of an aromatic hydrocarbon, still more preferably 80% or more by mass of an aromatic hydrocarbon.

When the acid catalyst contains sulfuric acid, and the organic solvent contains the aliphatic alcohol, the sulfuric acid reacts with the aliphatic alcohol and forms a monoalkyl sulfate, which can also act as a catalysis. Thus, when the acid catalyst contains sulfuric acid, the organic solvent preferably contains the aliphatic alcohol. The aliphatic alcohol with an increased number of carbon atoms has increased lipophilicity, is less likely to be miscible with sulfuric acid, and is less likely to produce a monoalkyl sulfate. Thus, the number of carbon atoms is preferably 8 or less.

Thus, reacting sulfuric acid with the aliphatic alcohol to form a monoalkyl sulfate can control the acid strength of the acid catalyst and suppress condensation (oligomerization) and coloration of the raw material ketone or aldehyde. This enables convenient and efficient production of the bisphenol with less by-products and less coloration.

When sulfuric acid is reacted with the aliphatic alcohol to form a monoalkyl sulfate, and the catalytic action of the monoalkyl sulfate is also utilized, a low mole ratio of the aliphatic alcohol to the sulfuric acid (the number of moles of the aliphatic alcohol/the number of moles of the sulfuric acid) results in significant condensation (oligomerization) and coloration of the raw material ketone or aldehyde. A high mole ratio results in a decrease in the concentration of sulfuric acid and a slow reaction. Thus, the mole ratio of the aliphatic alcohol to sulfuric acid is preferably 0.01 or more, more preferably 0.05 or more, still more preferably 0.1 or more, and preferably 10 or less, more preferably 5 or less, still more preferably 3 or less.

Thus, the organic solvent may contain the aromatic hydrocarbon and the aliphatic alcohol, for example. The organic solvent may contain 1% to 95% by mass of the aromatic hydrocarbon and 0.1% to 10% by mass of the aliphatic alcohol.
(Preparation of Reaction Liquid)

The reaction liquid may be prepared by any method, for example, by supplying an acid catalyst to a liquid mixture of an aromatic alcohol, an organic solvent, and a ketone or aldehyde, or by supplying a ketone or aldehyde to a liquid mixture of an acid catalyst, an aromatic alcohol, and an organic solvent.

To suppress the oligomerization of the ketone or aldehyde by self-condensation, a solution containing an aromatic alcohol, an acid catalyst, and an organic solvent is preferably mixed with a solution containing the ketone or aldehyde. In this case, the solution containing the ketone or aldehyde may contain the ketone or aldehyde alone or may also contain a thiol and/or an organic solvent. The solution containing the ketone or aldehyde preferably contains a thiol.
(Reaction Conditions)

The bisphenol C producing reaction is a condensation reaction. An excessively high reaction temperature of the production reaction results in promoted oxidative decomposition of the thiol, and an excessively low reaction temperature results in a longer reaction time. Thus, the reaction temperature preferably ranges from 0° C. to 50° C.

An excessively long reaction time of the production reaction results in the decomposition of the bisphenol. Thus, the reaction time is preferably 30 hours or less, more preferably 25 hours or less, still more preferably 20 hours or less. The lower limit of the reaction time is typically 0.5 hours or more.

The reaction can be stopped by adding water in an amount equal to or more than the amount of sulfuric acid used or by adding aqueous sodium hydroxide such that the sulfuric acid concentration is 45% or less by mass to decrease the sulfuric acid concentration.

(Purification)

The bisphenol C product produced by the bisphenol C producing reaction can be purified in the usual manner. For example, the bisphenol product can be purified by a convenient means, such as crystallization or column chromatography. More specifically, after the condensation reaction, an organic phase prepared by separating the reaction liquid is washed with water, saline, or the like, and if necessary is neutralized and washed with aqueous sodium hydrogen carbonate or the like. The washed organic phase is then cooled and crystallized. When a large amount of aromatic alcohol is used, excess aromatic alcohol is distilled off before the crystallization.

In the present embodiment, the trimethyl bisphenol A produced as a by-product in the bisphenol C producing reaction system is left to produce a bisphenol C product containing the trimethyl bisphenol A as the bisphenol composition according to the present invention. Thus, in the method for purifying the bisphenol C product, for example, crystallization, suspension washing, and sprinkling washing are appropriately combined to modify the purification conditions such that a predetermined amount of the trimethyl bisphenol A remains in the purified bisphenol C product.

(Example of Purification Step)

As an example of the purification step suitable for the present invention, a purification method of washing the bisphenol C product produced by the condensation reaction in a washing step and then performing precipitation in a crystallization step is described below.

In this case, after the condensation reaction, the organic phase containing the bisphenol C formed from the reaction liquid is washed with demineralized water, and the washed organic phase is cooled and crystallized. Washing is performed multiple times as described below. Crystallization may also be performed multiple times.

<Washing Step>

The washing step includes at least a first step and a second step described below.

First step: The bisphenol C-containing organic phase (O1) formed in the reaction step is mixed with demineralized water and is then phase-separated into a bisphenol C-containing organic phase (O2) and an aqueous phase (W1). The aqueous phase (W1) is removed to obtain the bisphenol C-containing organic phase (O2).

Second step: The bisphenol C-containing organic phase (O2) formed in the first water washing step is mixed with demineralized water and is then phase-separated into a bisphenol C-containing organic phase (O3) and an aqueous phase (W2). The aqueous phase (W2) is removed to obtain the bisphenol C-containing organic phase (O3).

The first step is preferably performed such that the aqueous phase (W1) has a pH of 8.5 or more. The second step is preferably performed such that the aqueous phase (W2) has an electrical conductivity of 10 µS/cm.

The demineralized water is water with an electrical conductivity of 1.5 µS/cm or less, such as ion-exchanged water or pure water.

The measurement temperature of the aqueous phase (W1) is preferably room temperature (20° C. to 30° C.), for example, 25° C.

When the aqueous phase has a pH of less than 7, washing with a basic substance, such as sodium hydroxide or sodium hydrogen carbonate, can be followed by washing with water. The organic phase washed with the basic substance is washed again with water such that the aqueous phase has a pH of 8.5 or more. The washing effect is small when the aqueous phase (W1) has low basicity (low pH). Thus, the pH is preferably 8.5 or more, more preferably 9 or more. When the aqueous phase (W1) has high basicity (high pH), however, the bisphenol C becomes a bisphenol C salt, and the loss in washing with water increases. Thus, the upper limit of the pH of the aqueous phase (W1) is typically 14 or less, preferably 13 or less, more preferably 12 or less.

The measurement temperature of the electrical conductivity of the aqueous phase (W2) in the second water washing step is preferably room temperature (20° C. to 30° C.), for example, 25° C.

The electrical conductivity of the aqueous phase (W2) in the second water washing step is preferably 10 µS/cm or less, more preferably 9 µS/cm or less, still more preferably 8 µS/cm or less.

In the washing step, preferably, the aqueous phase first formed by washing the bisphenol-containing organic phase with water has a pH of 8.5 or more and is basic, the washing is repeated if necessary, and the aqueous phase is subjected to the crystallization step when the aqueous phase has an electrical conductivity of 10 µS/cm or less.

Washing with demineralized water such that the aqueous phase (W1) in the first water washing step has a pH equal to or higher than the lower limit and the aqueous phase (W2) in the second water washing step has an electrical conductivity equal to or lower than the upper limit and thereby effectively removing impurities, such as by-products, a residual catalyst, and a residual thiol, from the bisphenol product can produce a bisphenol composition with a good hue, with a high polymerization reaction efficiency when used as a raw material bisphenol for a polycarbonate resin, and capable of producing a polycarbonate resin with a good hue. In particular, in the condensation reaction including a thiol as a promoter, an acidic thionium is produced from the thiol, and the acidic thionium in the bisphenol composition inhibits the polymerization reaction in the production of the polycarbonate resin. The washing step in which the pH of the aqueous phase (W1) and the electrical conductivity of the aqueous phase (W2) are controlled as described above can efficiently remove the thionium and prevent the thionium from inhibiting the polymerization.

The temperature in the washing step is preferably 90° C. or less, particularly preferably 85° C. or less, and 50° C. or more, particularly preferably 55° C. or more, so that the bisphenol can be efficiently precipitated by cooling in the crystallization step described later without evaporating the solvent. Each washing time (the time for adding demineralized water to the organic phase and mixing them) is typically approximately 1 to 120 minutes.

<Crystallization Step>

The cooling temperature in the crystallization step is preferably lower by 10° C. to 120° C. than the temperature of the organic phase (O3) formed in the washing step and is preferably 40° C. or less, particularly preferably 30° C. or less, and preferably −20° C. or more, particularly preferably −10° C. or more. Cooling the washed organic phase (O3) to such a temperature can efficiently precipitate the bisphenol composition.

The bisphenol composition precipitated in the crystallization step can be recovered by solid-liquid separation, such as filtration, centrifugation, or decantation.

Even when the washing step and the crystallization step are performed, the purification conditions are preferably controlled such that the bisphenol (II) remains at a predetermined ratio in the bisphenol composition after the purification.

<Applications of Bisphenol>

The bisphenol composition according to the present invention can be used as a constituent of various thermoplastic resins, such as polyether resins, polyester resins, polyarylate resins, polycarbonate resins, polyurethane resins, and acrylic resins, and various thermosetting resins, such as epoxy resins, unsaturated polyester resins, phenolic resins, polybenzoxazine resins, and cyanate resins, a curing agent, an additive agent, or a precursor thereof, for use in various applications, such as optical materials, recording materials, insulating materials, transparent materials, electronic materials, adhesive materials, and heat-resistant materials. The bisphenol composition according to the present invention is also useful as a developer or an antifading agent for thermal recording materials, a bactericide, an antimicrobial and fungicidal agent, or another additive agent.

The bisphenol composition according to the present invention can impart good mechanical properties and is therefore preferably used as a raw material (monomer) for thermoplastic resins and thermosetting resins, particularly preferably as a raw material for polycarbonate resins and epoxy resins. The bisphenol composition according to the present invention is also preferably used as a developer, more preferably used in combination with a leuco dye or a color change temperature regulator.

[Polycarbonate Resin]

The polycarbonate resin according to the present invention is a polycarbonate resin having at least a repeating structural unit represented by the following general formula (A). A compound produced by alkaline hydrolysis of the polycarbonate resin (hereinafter also referred to as an "alkaline hydrolysate") contains the bisphenol (I) and the bisphenol (II). The bisphenol (II) produced by alkaline hydrolysis constitutes 160 mass ppm or more of the polycarbonate resin. The polycarbonate resin according to the present invention can be produced from the bisphenol composition according to the present invention.

[Chem. 12]

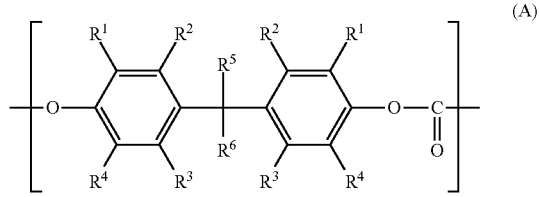

(A)

In the general formula (A), $R^1$ to $R^6$ have the same meaning as in the general formula (1).

When the bisphenol (II) content of the alkaline hydrolysate of the polycarbonate resin is below the lower limit with respect to the polycarbonate resin, the polycarbonate resin cannot have a good hue.

The ratio of the bisphenol (II) to the polycarbonate resin is preferably 200 mass ppm or more, more preferably 300 mass ppm or more, and preferably 20000 mass ppm or less, more preferably 15000 mass ppm or less.

The polycarbonate resin according to the present invention may be produced from the bisphenol composition according to the present invention by transesterification between the bisphenol composition according to the present invention and diphenyl carbonate or the like in the presence of an alkali metal compound and/or an alkaline-earth metal compound.

The bisphenol composition according to the present invention may contain only one bisphenol or two or more bisphenols (I), or one or more of bisphenol (I) and other bisphenols. Two or more bisphenols can be used to produce a copolymerized polycarbonate resin. A dihydroxy compound other than the bisphenol composition according to the present invention may be used in combination for the reaction.

The transesterification can be performed by an appropriately selected known method. An example of a method for producing a polycarbonate resin using the bisphenol composition according to the present invention and diphenyl carbonate as raw materials is described below.

In the method for producing a polycarbonate resin, an excessive amount of diphenyl carbonate is preferably used relative to the bisphenol in the bisphenol composition according to the present invention. A large amount of diphenyl carbonate relative to the bisphenol is preferably used to produce a polycarbonate resin with fewer terminal hydroxy groups and with high thermal stability. A small amount of diphenyl carbonate relative to the bisphenol is preferably used to increase the transesterification rate and to easily produce a polycarbonate resin with a desired molecular weight. Thus, the amount of diphenyl carbonate per mole of the bisphenol is typically 1.001 mol or more, preferably 1.002 mol or more, and typically 1.3 mol or less, preferably 1.2 mol or less.

With respect to a method for supplying raw materials, although the bisphenol composition according to the present invention and diphenyl carbonate can be supplied in a solid state, one or both of them are preferably melted and supplied in a liquid state.

A transesterification catalyst is typically used to produce a polycarbonate resin by transesterification between diphenyl carbonate and a bisphenol. In the method for producing a polycarbonate resin, the transesterification catalyst is preferably an alkali metal compound and/or an alkaline-earth metal compound. These may be used alone, or two or more of them may be used in any combination and at any ratio. Practically, it is desirable to use an alkali metal compound.

The amount of the catalyst used is typically 0.05 μmol or more, preferably 0.08 μmol or more, more preferably 0.10 μmol or more, and typically 100 μmol or less, preferably 50 μmol or less, more preferably 20 μmol or less, per mole of the bisphenol or diphenyl carbonate.

When the amount of the catalyst used is in the above range, it is easy to have polymerization activity necessary to produce a polycarbonate resin with a desired molecular weight, and the polycarbonate resin has a good hue, does not have excessive branching, and easily has good fluidity while forming.

To produce a polycarbonate resin by the above method, preferably, both raw materials are continuously supplied to a raw material mixing tank, and the resulting mixture and the transesterification catalyst are continuously supplied to a polymerization vessel.

In the production of a polycarbonate resin by transesterification, both raw materials supplied to the raw material mixing tank are typically uniformly stirred and then supplied to the polymerization vessel to which the transesterification catalyst is added to produce the polymer.

In the production of a polycarbonate resin from the bisphenol composition according to the present invention, the polymerization reaction temperature is preferably 80° C. or more, particularly preferably 150° C. or more, and preferably 400° C. or less, particularly preferably 350° C. or less. The polymerization time is appropriately adjusted for the ratio of the raw materials, the desired molecular weight of the polycarbonate resin, or the like. A long polymerization time results in poor quality, such as poor color tone. Thus, the polymerization time is preferably 10 hours or less, more preferably 8 hours or less. The lower limit of the polymerization time is typically 0.1 hours or more or 0.3 hours or more.

A polycarbonate resin with a good hue and high transparency can be produced from the bisphenol composition according to the present invention. For example, a polycarbonate resin with a viscosity-average molecular weight (Mv) of 10,000 or more, preferably 15,000 or more, and 100,000 or less, preferably 35,000 or less, with a pellet YI of 10 or less, and with a good hue and high transparency can be produced in a short time.

EXAMPLES

The present invention is more specifically described in the following examples and comparative examples. The present invention is not limited to these examples as long as it does not depart from the gist thereof.

[Raw Materials and Reagents]

In the following examples and comparative examples, ortho-cresol, toluene, 2,6-xylenol, sodium hydroxide, sulfuric acid, dodecanethiol, acetone, sodium hydrogen carbonate, cesium carbonate, acetonitrile, methylene chloride, acetic acid, and ammonium acetate were reagents manufactured by FUJIFILM Wako Pure Chemical Corporation.

As the cresol, a reagent manufactured by FUJIFILM Wako Pure Chemical Corporation, a product manufactured by LANXESS, or a product manufactured by JFE Chemical Industries, Ltd. was used.

Diphenyl carbonate was a product manufactured by Mitsubishi Chemical Corporation.

[Analysis]

<Composition of Bisphenol C Production Reaction Liquid, Analysis of Trimethyl bisphenol A in Bisphenol C Composition, and Analysis of Trimethyl bisphenol A in Alkaline Hydrolysate of Polycarbonate Resin>

The composition analysis of a bisphenol C production reaction liquid, the analysis of the trimethyl bisphenol A in a bisphenol C composition, and the analysis of the trimethyl bisphenol A in an alkaline hydrolysate of a polycarbonate resin were performed by high-performance liquid chromatography by the following procedures under the following conditions.

Apparatus: "LC-2010A" manufactured by Shimadzu Corporation
  Imtakt Scherzo SM-C18 3 μm 250 mm×3.0 mm ID
  Low-pressure gradient method
  Analysis temperature: 40° C.
  Eluent composition:
  Solution A: A solution of ammonium acetate:acetic acid:demineralized water=3.000 g:1 mL:1 L
  Solution B: A solution of ammonium acetate:acetic acid:acetonitrile:demineralized water=1.500 g:1 mL:900 mL:150 mL At an analysis time of 0 minutes, the eluent composition was liquid A:liquid B=60:40 (volume ratio, the same applies hereinafter).
  At an analysis time in the range of 0 to 41.67 minutes, the eluent composition was gradually changed to liquid A:liquid B=10:90.
  At an analysis time in the range of 41.67 to 50 minutes, liquid A:liquid B=10:90 was maintained.
  The analysis was performed at a flow rate of 0.34 mL/min.

<Preparation of Analysis Solution of Trimethyl Bisphenol A in Alkaline hydrolysate of Polycarbonate Resin>

0.5 g of polycarbonate resin pellets and 5 mL of methylene chloride were added to a 100-mL Erlenmeyer flask with a stirring bar to prepare a homogeneous solution. 45 mL of methanol and then 5 mL of 25% aqueous sodium hydroxide were added to the solution. The Erlenmeyer flask was immersed in a water bath at 70° C. to 75° C., and the solution was stirred for 30 minutes. The Erlenmeyer flask was then taken out of the water bath. The solution was neutralized with hydrochloric acid. Water and methanol were added to the solution, and the solution was made homogeneous to prepare an analysis solution. The analysis solution was subjected to measurement by high-performance liquid chromatography.

<Molecular Weight Measurement of Trimethyl Bisphenol A>

The molecular weights of the Trimethyl bisphenol A were determined by high-performance liquid chromatograph mass spectrometry (LCMS). The high-performance liquid chromatograph mass spectrometry (LCMS) was performed by the following procedures under the following conditions.

Separator: "Agilent 1200" manufactured by Agilent Technologies
  Imtakt Scherzo SM-C18 3 μm 150 mm×4.6 mm ID
  Low-pressure gradient method
  Analysis temperature: 40° C.
  Eluent composition:
  Liquid A: A solution of ammonium acetate:acetic acid:demineralized water=3.000 g:1 mL:1 L
  Liquid B: A solution of ammonium acetate:acetic acid:acetonitrile=1.500 g:1 mL:1 L
  At an analysis time of 0 minutes, the eluent composition was liquid A:liquid B=60:40 (volume ratio, the same applies hereinafter).
  At an analysis time in the range of 0 to 25 minutes, the eluent composition was gradually changed to liquid A:liquid B=90:10.
  At an analysis time in the range of 25 to 30 minutes, liquid A:liquid B=90:10 was maintained.
  The analysis was performed at a flow rate of 1.0 mL/min.
  Detection wavelength: 280 nm
  Mass spectrometer: "Agilent LC/MS 6130" manufactured by Agilent Technologies
  Ion source: ESI (Positive/Negative) with AJS probe <Analysis of Bisphenol C in Bisphenol C Composition>

Bisphenol C in the bisphenol C composition was analyzed in the same manner as in <Composition of Bisphenol C Production Reaction Liquid, Analysis of Trimethyl bisphenol A in Bisphenol C Composition, and Analysis of Trimethyl bisphenol A in Alkaline Hydrolysate of Polycarbonate Resin>.

In a bisphenol C composition produced in the present invention, the bisphenol C purity of the bisphenol is typically 99% or more by mass, and the amount of bisphenol produced other than the bisphenol C is very small. Thus, the bisphenol C content of the bisphenol C composition can be considered to be the bisphenol content.

<Identification of Isopropenyl Cresol>

Isopropenyl cresol was identified with a gas chromatograph mass spectrometer by the following procedures under the following conditions.

Apparatus: "Agilent 6890" manufactured by Agilent Technologies

Column: "DB-1MS" manufactured by Agilent Technologies (inner diameter 0.25 mm×30 m×0.25 μm)

Carrier gas: helium

Flow rate: 1 cm³/min

Inlet temperature: 280° C.

Transfer temperature: 250° C.

Ion source temperature: 250° C.

Temperature rise pattern of column: The temperature was first held at 50° C. for 3 minutes, was then increased to 320° C. at 10° C./min, and was held at 280° C. for 5 minutes.

<pH Measurement>

The pH of a 25° C. aqueous phase taken out of the flask was measured with a pH meter "pH METER ES-73" manufactured by Horiba, Ltd.

<Electrical Conductivity>

The electrical conductivity of a 25° C. aqueous phase taken out of the flask was measured with an electrical conductivity meter "COND METER D-71" manufactured by Horiba, Ltd.

<Methanol Dissolution Color of Bisphenol C Composition>

The methanol dissolution color of the bisphenol C composition was evaluated by measuring the Hazen color number of a homogeneous solution of 10 g of the bisphenol C composition and 10 g of methanol in a test tube "P-24" (24 mmφ×200 mm) manufactured by Nichiden Rika Glass Co., Ltd. using "SE 6000" manufactured by Nippon Denshoku Industries Co., Ltd. at room temperature (approximately 20° C.).

<Molten color of Bisphenol C Composition>

The molten color of the bisphenol C composition was evaluated by melting 20 g of the bisphenol C composition at 190° C. for 30 minutes in a test tube "P-24" (24 mmφ×200 mm) manufactured by Nichiden Rika Glass Co., Ltd. and measuring the Hazen color number of the bisphenol C composition with "SE 6000" manufactured by Nippon Denshoku Industries Co., Ltd.

<Thermal Color Tone Stability of Bisphenol C Composition>

The thermal color tone stability of the bisphenol C composition was evaluated by melting 20 g of the bisphenol C composition at 190° C. for 4 hours in a test tube "P-24" (24 mmφ×200 mm) manufactured by Nichiden Rika Glass Co., Ltd. and measuring the Hazen color number of the bisphenol C composition with "SE 6000" manufactured by Nippon Denshoku Industries Co., Ltd.

<Thermal Decomposition Stability of Bisphenol C Composition>

The thermal decomposition stability of the bisphenol C composition was evaluated by melting 20 g of the bisphenol C composition at 190° C. for 2 hours in a test tube "P-24" (24 mmφ×200 mm) manufactured by Nichiden Rika Glass Co., Ltd. and measuring the amount of produced isopropenyl cresol in the same manner as in the composition analysis of the bisphenol C production reaction liquid.

<Analysis of Sodium, Iron and Aluminum in Bisphenol C Composition>

Approximately 1 g of the bisphenol C composition was collected and was then dry-ashed after the addition of sulfuric acid. Hydrofluoric acid was then added to the resulting sample, and the sample was dried. Nitric acid and pure water were then added for dissolution. After the volume of the resulting sample was made constant, the sample was appropriately diluted, and sodium, iron and aluminum in the bisphenol C composition were quantitatively determined with an ICP-MS ("ELEMENT 2" manufactured by Thermo Fisher Scientific Inc.)

<Viscosity-Average Molecular Weight>

The polycarbonate resin was dissolved in methylene chloride (concentration: 6.0 g/L). The specific viscosity ($\eta$sp) was measured at 20° C. with a Ubbelohde viscosity tube. The viscosity-average molecular weight (Mv) was calculated using the following formula.

$$\eta sp/C=[\eta](1+0.28\eta sp)$$

$$[\eta]=1.23\times 10^{-4}\,Mv^{0.83}$$

<Pellet YI>

The pellet YI (the transparency of the polycarbonate resin) was evaluated by measuring the YI (yellowness index) of reflected light from polycarbonate resin pellets in accordance with ASTM D1925. A spectrophotometer "CM-5" manufactured by Konica Minolta Inc. was used as an apparatus. The measurement conditions include a measurement diameter of 30 mm, and SCE was selected.

A Petri dish measurement calibration glass "CM-A212" was inserted into a measurement section and was covered with a zero calibration box "CM-A124" for zero calibration. A built-in white calibration plate was then used for white calibration. Measurement was then performed with a white calibration plate "CM-A210". L* was 99.40±0.05, a* was 0.03±0.01, b* was −0.43±0.01, and YI was −0.58±0.01.

A cylindrical glass vessel with an inner diameter of 30 mm and a height of 50 mm was filled with pellets to a depth of approximately 40 mm to measure the YI. The operation of taking the pellets out of the glass vessel and performing measurement again was repeated twice, and three measurements in total was averaged.

Reference Example 1

A 500-mL recovery flask equipped with a stirring bar, a thermometer, and a distillation apparatus was charged with 85 g of the bisphenol C composition and 4.5 g of sodium hydroxide and was immersed in an oil bath heated to 195° C. After the bisphenol C in the recovery flask melted, the pressure in the flask was gradually decreased to full vacuum with a vacuum pump. After a while, evaporation started, and vacuum distillation was performed until distillation was completed. Gas chromatography with a mass detector showed that the resulting fraction was a mixture of cresol and isopropenyl cresol produced by the thermal decomposition of bisphenol C. The fraction was used to determine the retention time of isopropenyl cresol under the composition analysis conditions of the bisphenol C production reaction liquid.

Example 1

(1) Preparation of First Liquid Mixture

A separable flask equipped with a thermometer, a dropping funnel, a jacket, and an anchor-shaped impeller blade was charged with 320 g of toluene, 15 g of methanol, and 230 g (2.13 mol) of ortho-cresol manufactured by FUJIFILM Wako Pure Chemical Corporation (reagent) in a nitrogen atmosphere. The internal temperature was set at 10° C. or less. Subsequently, 95 g of 98% by weight sulfuric acid was slowly added for 0.3 hours while stirring, and the mixture was cooled to 5° C. or less.

(2) Preparation of Second Liquid Mixture 50 g of toluene, 65 g (1.12 mol) of acetone, and 5.4 g of dodecanethiol were mixed in a 500-mL Erlenmeyer flask to prepare a second liquid mixture (dropping liquid).

(3) Preparation of Reaction Liquid

After the internal temperature of the first liquid mixture was decreased to 5° C. or less, the second liquid mixture was supplied over 1 hour through the dropping funnel such that the internal temperature was not increased to 10° C. or more. Thus, a reaction liquid was prepared.

(4) Reaction

The reaction liquid was stirred at an internal temperature of 10° C. for 2.5 hours.

(5) Purification (Washing)

After completion of the reaction, 190 g of 25% aqueous sodium hydroxide was supplied to the product, and the product was heated to 80° C. After the temperature reached 80° C., the product was allowed to stand, and a lower aqueous phase was extracted. The resulting first organic phase was mixed with 400 g of demineralized water for 30 minutes and was allowed to stand, and the aqueous phase was removed. The resulting second organic phase was mixed with 120 g of a 1.5% by mass sodium hydrogen carbonate solution for 30 minutes and was allowed to stand, and the lower phase was extracted. The resulting third organic phase was mixed with 120 g of a 1.5% by mass sodium hydrogen carbonate solution for 30 minutes and was allowed to stand, and the lower phase was extracted. The resulting fourth organic phase was extracted, and the mass of the fourth organic phase was determined to be 666 g.

Part of the fourth organic phase was taken out, and the composition of the fourth organic phase was determined by high-performance liquid chromatography: Ortho-cresol was 5.3% by mass (5.3% by mass×the mass of the organic phase 666 g÷the molecular weight of ortho-cresol 108 g/mol÷the amount of substance of charged ortho-cresol 2.1 mol=15.3% by mole), and bisphenol C was 31.5% by mass (31.5% by mass×the mass of the organic phase 666 g×2÷the molecular weight of bisphenol C 256 g/mol÷the amount of substance of charged ortho-cresol 2.1 mol=78.0% by mole).

(6) Purification (Washing with Water and Crystallization)

The fourth organic phase was mixed with 200 g of demineralized water for 30 minutes and was allowed to stand. A lower aqueous phase (first aqueous phase) was removed to obtain a fifth organic phase. The first aqueous phase had a pH of 9.7. The fifth organic phase was mixed with 200 g of demineralized water for 30 minutes and was allowed to stand. A lower aqueous phase (second aqueous phase) was removed to obtain a sixth organic phase. The sixth organic phase was mixed with 200 g of demineralized water for 30 minutes and was allowed to stand. A lower aqueous phase (third aqueous phase) was removed. The third aqueous phase had an electrical conductivity of 2.7 µS/cm.

The resulting sixth organic phase was cooled from 80° C. to 20° C. and was maintained at 20° C. to precipitate bisphenol C. After the temperature was decreased to 10° C. and reached 10° C., a crude wet cake was prepared by solid-liquid separation with a centrifugal separator. The wet cake was washed by sprinkling 500 g of toluene, and a purified wet cake was prepared by solid-liquid separation with a centrifugal separator. The purified wet cake was subjected to distillation under reduced pressure at an oil bath temperature of 100° C. with an evaporator equipped with an oil bath to distill off a low-boiling fraction. Thus, 190 g of a white bisphenol C composition was obtained.

In the measurement of the methanol dissolution color of the bisphenol C composition, the Hazen color number was 0. In the measurement of the molten color of the bisphenol C composition, the Hazen color number was 3. In the measurement of the thermal color tone stability of the bisphenol C composition, the Hazen color number was 26. In the measurement of the thermal decomposition stability of the bisphenol C composition, the amount of isopropenyl cresol produced was 186 mass ppm.

The quality of the bisphenol C composition was examined. A characteristic peak with a retention time of 24.12 minutes was detected with a high-performance liquid chromatograph. The component of this peak was identified as a trimethyl bisphenol A with a molecular weight of 270 g/mol and with a structure represented by the following structural formula (IIa) by high-performance liquid chromatography with a mass spectrometer.

[Chem. 13]

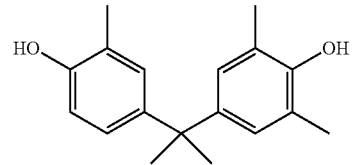

(IIa)

The bisphenol C composition had a trimethyl bisphenol A content of 210 mass ppm.

The bisphenol C composition had a bisphenol C content of 99.9% by mass.

The bisphenol C composition had sodium, iron, and aluminum contents of 0.04 mass ppm, 0.05 mass ppm, and 0.05 mass ppm, respectively.

Example 2

(1) Preparation of First Liquid Mixture

A separable flask equipped with a thermometer, a dropping funnel, a jacket, and an anchor-shaped impeller blade was charged with 320 g of toluene, 15 g of methanol, 5 g (0.04 mol) of 2,6-xylenol, and 225 g (2.08 mol) of ortho-cresol manufactured by FUJIFILM Wako Pure Chemical Corporation (reagent) in an air atmosphere. The internal temperature was set at 10° C. or less. Subsequently, 95 g of 98% by weight sulfuric acid was slowly added for 0.3 hours while stirring, and the mixture was cooled to 5° C. or less.

(2) Preparation of Second Liquid Mixture 50 g of toluene, 65 g (1.12 mol) of acetone, and 5.4 g of dodecanethiol were mixed in a 500-mL Erlenmeyer flask to prepare a second liquid mixture (dropping liquid).

(3) Preparation of Reaction Liquid

After the internal temperature of the first liquid mixture was decreased to 5° C. or less, the second liquid mixture was supplied over 1 hour through the dropping funnel such that the internal temperature was not increased to 10° C. or more. Thus, a reaction liquid was prepared.

(4) Reaction

The reaction liquid was stirred at an internal temperature of 10° C. for 2.5 hours.

(5) Purification (Washing)

After completion of the reaction, 190 g of 25% aqueous sodium hydroxide was supplied to the product, and the product was heated to 80° C. After the temperature reached 80° C., the product was allowed to stand, and a lower aqueous phase was extracted. The resulting first organic phase was mixed with 400 g of demineralized water for 30 minutes and was allowed to stand, and the aqueous phase was removed. The resulting second organic phase was mixed with 120 g of a 1.5% by mass sodium hydrogen carbonate solution for 30 minutes and was allowed to stand, and the lower phase was extracted. The resulting third organic phase mixed with 120 g of a 1.5% by mass sodium hydrogen carbonate solution for 30 minutes and was allowed to stand, and the lower phase was extracted. The resulting fourth organic phase was extracted, and the mass of the fourth organic phase was determined to be 666 g.

Part of the fourth organic phase was taken out, and the composition of the fourth organic phase was determined by high-performance liquid chromatography: Ortho-cresol was 5.8% by mass (5.8% by mass×the mass of the organic phase 666 g÷the molecular weight of ortho-cresol 108 g/mol÷the amount of substance of charged ortho-cresol 2.08 mol=17.2% by mole), and bisphenol C was 29.4% by mass (29.4% by mass×the mass of the organic phase 666 g×2÷the molecular weight of bisphenol C 256 g/mol÷the amount of substance of charged ortho-cresol 2.08 mol=73.5% by mole).

(6) Purification (Washing with Water and Crystallization)

The fourth organic phase was mixed with 200 g of demineralized water for 30 minutes and was allowed to stand. A lower aqueous phase (first aqueous phase) was removed to obtain a fifth organic phase. The first aqueous phase had a pH of 9.7. The fifth organic phase was mixed with 200 g of demineralized water for 30 minutes and was allowed to stand. A lower aqueous phase (second aqueous phase) was removed to obtain a sixth organic phase. The sixth organic phase was mixed with 200 g of demineralized water for 30 minutes and was allowed to stand. A lower aqueous phase (third aqueous phase) was removed. The third aqueous phase had an electrical conductivity of 2.7 µS/cm.

The resulting sixth organic phase was cooled from 80° C. to 20° C. and was maintained at 20° C. to precipitate bisphenol C. After the temperature was decreased to 10° C. and reached 10° C., a crude wet cake was prepared by solid-liquid separation with a centrifugal separator. The wet cake was washed by sprinkling 500 g of toluene, and a purified wet cake was prepared by solid-liquid separation with a centrifugal separator. The purified wet cake was subjected to distillation under reduced pressure at an oil bath temperature of 100° C. with an evaporator equipped with an oil bath to distill off a low-boiling fraction. Thus, 178 g of a white bisphenol C composition was obtained.

The bisphenol C composition had a bisphenol C content of 99.7% by mass, and trimethyl bisphenol A content of 20000 mass ppm.

In the measurement of the methanol dissolution color of the bisphenol C composition, the Hazen color number was 0. In the measurement of the molten color of the bisphenol C composition, the Hazen color number was 8. In the measurement of the thermal color tone stability of the bisphenol C composition, the Hazen color number was 32. In the measurement of the thermal decomposition stability of the bisphenol C composition, the amount of isopropenyl cresol produced was 166 mass ppm.

The sodium, iron and aluminum contents of the bisphenol C composition were determined to be 0.02 mass ppm, 0.06 mass ppm and 0.04 mass ppm, respectively.

Comparative Example 1

(1) Preparation of First Liquid Mixture

A separable flask equipped with a thermometer, a dropping funnel, a jacket, and an anchor-shaped impeller blade was charged with 320 g of toluene, 15 g of methanol, and 230 g (2.13 mol) of ortho-cresol manufactured by LANXESS in a nitrogen atmosphere. The internal temperature was set at 10° C. or less. Subsequently, 95 g of 98% by weight sulfuric acid was slowly added for 0.3 hours while stirring, and the mixture was cooled to 5° C. or less.

(2) Preparation of Second Liquid Mixture 50 g of toluene, 65 g (1.12 mol) of acetone, and 5.4 g of dodecanethiol were mixed in a 500-mL Erlenmeyer flask to prepare a second liquid mixture (dropping liquid).

(3) Preparation of Reaction Liquid

After the internal temperature of the first liquid mixture was decreased to 5° C. or less, the second liquid mixture was supplied over 1 hour through the dropping funnel such that the internal temperature was not increased to 10° C. or more. Thus, a reaction liquid was prepared.

(4) Reaction

The reaction liquid was stirred at an internal temperature of 10° C. for 2 hours.

(5) Purification (Washing)

After completion of the reaction, 190 g of 25% aqueous sodium hydroxide was supplied to the product, and the product was heated to 80° C. After the temperature reached 80° C., the product was allowed to stand, and a lower aqueous phase was extracted. The resulting first organic phase was mixed with 400 g of demineralized water for 30 minutes and was allowed to stand, and the aqueous phase was removed. The resulting second organic phase was mixed with 120 g of a 1.5% by mass sodium hydrogen carbonate solution for 30 minutes and was allowed to stand, and the lower phase was extracted. The resulting third organic phase was mixed with 120 g of a 1.5% by mass sodium hydrogen carbonate solution for 30 minutes and was allowed to stand, and the lower phase was extracted. The resulting fourth organic phase was extracted, and the mass of the fourth organic phase was determined to be 666 g.

Part of the fourth organic phase was taken out, and the composition of the fourth organic phase was determined by high-performance liquid chromatography: Ortho-cresol was 5.3% by mass (5.3% by mass×the mass of the organic phase 666 g÷the molecular weight of ortho-cresol 108 g/mol÷the amount of substance of charged ortho-cresol 2.1 mol=15.3% by mole), and bisphenol C was 31.5% by mass (31.5% by mass×the mass of the organic phase 666 g×2÷the molecular weight of bisphenol C 256 g/mol÷the amount of substance of charged ortho-cresol 2.1 mol=78.0% by mole).

(6) Purification (Washing with Water and Crystallization)

The fourth organic phase was cooled from 80° C. to 20° C. and was maintained at 20° C. to precipitate bisphenol C. After the temperature was decreased to 10° C. and reached 10° C., a crude wet cake was prepared by solid-liquid separation with a centrifugal separator.

A separable flask equipped with a thermometer, a dropping funnel, a jacket, and an anchor-shaped impeller blade was charged with the whole crude wet cake and 420 g of toluene in a nitrogen atmosphere and was heated to 80° C. to prepare a homogeneous solution. The homogeneous solution was mixed with 200 g of demineralized water for 30 minutes and was allowed to stand. A lower aqueous phase (first aqueous phase) was removed to obtain a fifth organic phase. The first aqueous phase had a pH of 9.2. The fifth organic phase was mixed with 200 g of demineralized water for 30 minutes and was allowed to stand. A lower aqueous phase (second aqueous phase) was removed to obtain a sixth organic phase. The sixth organic phase was mixed with 200 g of demineralized water for 30 minutes and was allowed to stand. A lower aqueous phase (third aqueous phase) was removed to obtain a seventh organic phase. The third aqueous phase had an electrical conductivity of 2.3 μS/cm.

The seventh organic phase was cooled from 80° C. to 20° C. and was maintained at 20° C. to precipitate bisphenol C. After the temperature was decreased to 10° C. and reached 10° C., a wet cake was prepared by solid-liquid separation with a centrifugal separator. The wet cake was washed by sprinkling 200 g of toluene, and a purified wet cake was prepared by solid-liquid separation with a centrifugal separator. The purified wet cake was subjected to distillation under reduced pressure at an oil bath temperature of 100° C. with an evaporator equipped with an oil bath to distill off a low-boiling fraction. Thus, 183 g of a white bisphenol C composition was obtained.

The bisphenol C composition had a bisphenol C content of 99.9% by mass, and trimethyl bisphenol A was not detected (quantification limit was less than 0.1 mass ppm).

In the measurement of the methanol dissolution color of the bisphenol C composition, the Hazen color number was 3. In the measurement of the molten color of the bisphenol C composition, the Hazen color number was 48. In the measurement of the thermal color tone stability of the bisphenol C composition, the Hazen color number was 120. In the measurement of the thermal decomposition stability of the bisphenol C, the amount of isopropenyl cresol produced was 485 mass ppm.

The sodium, iron and aluminum contents of the bisphenol C composition were determined to be 0.22 mass ppm, 0.89 mass ppm and 0.12 mass ppm, respectively.

Comparative Example 2

A reagent bisphenol C manufactured by FUJIFILM Wako Pure Chemical Corporation had a trimethyl bisphenol A of 185 mass ppm.

In the measurement of the methanol dissolution color of the reagent bisphenol C, the Hazen color number was 20. In the measurement of the molten color of the reagent bisphenol C, the Hazen color number was 46. In the measurement of the thermal color tone stability of the reagent bisphenol C, the Hazen color number was 114. In the measurement of the thermal decomposition stability of the reagent bisphenol C, the amount of isopropenyl cresol produced was 585 mass ppm.

The sodium, iron and aluminum contents of the bisphenol C composition were measured to be 0.81 mass ppm, 1.22 mass ppm and 0.23 mass ppm, respectively.

Comparative Example 3

(1) Preparation of First Liquid Mixture

A separable flask equipped with a thermometer, a dropping funnel, a jacket, and an anchor-shaped impeller blade was charged with 320 g of toluene, 15 g of methanol, and 230 g (2.13 mol) of ortho-cresol manufactured JFE Chemical Industries, Ltd. in a nitrogen atmosphere. The internal temperature was set at 10° C. or less. Subsequently, 95 g of 98% by weight sulfuric acid was slowly added for 0.3 hours while stirring, and the mixture was cooled to 5° C. or less.

(2) Preparation of Second Liquid Mixture 50 g of toluene, 65 g (1.12 mol) of acetone, and 5.4 g of dodecanethiol were mixed in a 500-mL Erlenmeyer flask to prepare a second liquid mixture (dropping liquid).

(3) Preparation of Reaction Liquid

After the internal temperature of the first liquid mixture was decreased to 5° C. or less, the second liquid mixture was supplied over 1 hour through the dropping funnel such that the internal temperature was not increased to 10° C. or more. Thus, a reaction liquid was prepared.

(4) Reaction

The reaction liquid was stirred at an internal temperature of 10° C. for 2 hours.

(5) Purification (Washing)

After completion of the reaction, 190 g of 25% aqueous sodium hydroxide was supplied to the product, and the product was heated to 80° C. After the temperature reached 80° C., the product was allowed to stand, and a lower aqueous phase was extracted. The resulting first organic phase was mixed with 400 g of demineralized water for 30 minutes and was allowed to stand, and the aqueous phase was removed. The resulting second organic phase was mixed with 120 g of a 1.5% by mass sodium hydrogen carbonate solution for 30 minutes and was allowed to stand, and the lower phase was extracted. The resulting third organic phase was mixed with 120 g of a 1.5% by mass sodium hydrogen carbonate solution for 30 minutes and was allowed to stand, and the lower phase was extracted. The resulting fourth organic phase was extracted, and the mass of the fourth organic phase was determined to be 666 g.

Part of the fourth organic phase was taken out, and the composition of the fourth organic phase was determined by high-performance liquid chromatography: Ortho-cresol was 6.3% by mass (6.3% by mass×the mass of the organic phase 666 g÷the molecular weight of ortho-cresol 108 g/mol÷the amount of substance of charged ortho-cresol 2.1 mol=18.5% by mole), and bisphenol C was 28.4% by mass (28.4% by mass×the mass of the organic phase 666 g×2÷the molecular weight of bisphenol C 256 g/mol÷the amount of substance of charged ortho-cresol 2.1 mol=70.4% by mole).

(6) Purification (Washing with Water and Crystallization)

The fourth organic phase was cooled from 80° C. to 20° C. and was maintained at 20° C. to precipitate bisphenol C. After the temperature was decreased to 10° C. and reached 10° C., a crude wet cake was prepared by solid-liquid separation with a centrifugal separator.

A separable flask equipped with a thermometer, a dropping funnel, a jacket, and an anchor-shaped impeller blade was charged with the whole crude wet cake and 420 g of toluene in a nitrogen atmosphere and was heated to 80° C. to prepare a homogeneous solution. The homogeneous solution was mixed with 200 g of demineralized water for 30 minutes and was allowed to stand. A lower aqueous phase (first aqueous phase) was removed to obtain a fifth organic phase. The first aqueous phase had a pH of 9.3. The fifth organic phase was mixed with 200 g of demineralized water for 30 minutes and was allowed to stand. A lower aqueous phase (second aqueous phase) was removed to obtain a sixth organic phase. The sixth organic phase was mixed with 200 g of demineralized water for 30 minutes and was allowed to stand. A lower aqueous phase (third aqueous phase) was removed to obtain a seventh organic phase. The third aqueous phase had an electrical conductivity of 2.1 μS/cm.

The seventh organic phase was cooled from 80° C. to 20° C. and was maintained at 20° C. to precipitate bisphenol C. After the temperature was decreased to 10° C. and reached 10° C., a wet cake was prepared by solid-liquid separation with a centrifugal separator. The wet cake was washed by sprinkling 200 g of toluene, and a purified wet cake was prepared by solid-liquid separation with a centrifugal separator. The purified wet cake was subjected to distillation under reduced pressure at an oil bath temperature of 100° C. with an evaporator equipped with an oil bath to distill off a low-boiling fraction. Thus, 160 g of a white bisphenol C composition was obtained.

The bisphenol C composition had a bisphenol C content of 99.9% by mass and a trimethyl bisphenol A content of 55 mass ppm.

In the measurement of the methanol dissolution color of the bisphenol C composition, the Hazen color number was 2. In the measurement of the molten color of the bisphenol C composition, the Hazen color number was 39. In the measurement of the thermal color tone stability of the bisphenol C composition, the Hazen color number was 105. In the measurement of the thermal decomposition stability of the bisphenol C, the amount of isopropenyl cresol produced was 412 mass ppm.

The sodium, iron and aluminum contents of the bisphenol C composition were determined to be 0.07 mass ppm, 0.09 mass ppm and 0.08 mass ppm, respectively.

Table 1 summarizes the trimethyl bisphenol A content (bisphenol (II) content) of the bisphenol C composition, the methanol dissolution color, the molten color, the thermal color tone stability, the thermal decomposition stability, and the metal (sodium (Na), iron (Fe), and aluminum (Al)) contents in Examples 1 and 2 and Comparative Examples 1 to 3.

Table 1 shows that an trimethyl bisphenol A content of 150 mass ppm or more and 20,000 mass ppm or less results in improved methanol dissolution color, molten color, and thermal color tone stability. A trimethyl bisphenol A content of 150 mass ppm or more and 20,000 mass ppm or less also results in improved thermal decomposition stability.

the reaction vessel was decreased from 13.3 kPa to 399 Pa over 40 minutes to remove the distilled phenol from the system.

The external temperature of the reaction vessel was then increased to 280° C., the absolute pressure of the reaction vessel was decreased to 30 Pa, and the polycondensation reaction was performed. The polycondensation reaction was completed when the stirrer of the reaction vessel had a predetermined stirring power. The time from heating to 280° C. to the completion of polymerization (later stage polymerization time) was 210 minutes.

The reaction vessel was then repressurized with nitrogen to an absolute pressure of 101.3 kPa and then to a gauge pressure of 0.2 MPa. A polycarbonate resin was extracted as a strand from the bottom of the reaction vessel. Thus, a strand-like polycarbonate resin was obtained.

The strand was then pelletized with a rotary cutter to form polycarbonate resin pellets.

The polycarbonate resin had a viscosity-average molecular weight (Mv) of 24800 and a pellet YI of 6.9.

The trimethyl bisphenol A in the alkaline hydrolysate of the polycarbonate resin constituted 160 mass ppm of the polycarbonate resin.

Example 4

Example 4 was performed in the same manner as in Example 3 except that 100.00 g (bisphenol C 0.39 mol) of

TABLE 1

| | Trimethyl bisphenol A content | Metal content (mass ppm) | | | Methanol dissolution color | Molten color | Thermal color tone stability | Thermal decomposition stability |
|---|---|---|---|---|---|---|---|---|
| | (mass ppm) | Na | Fe | Al | (APHA) | (APHA) | (APHA) | (mass ppm) |
| Example 1 | 210 | 0.04 | 0.05 | 0.05 | 0 | 3 | 26 | 186 |
| Example 2 | 20000 | 0.02 | 0.06 | 0.04 | 0 | 8 | 32 | 166 |
| Comparative example 1 | <0.1 | 0.22 | 0.89 | 0.12 | 3 | 48 | 120 | 485 |
| Comparative example 2 | 185 | 0.81 | 1.22 | 0.23 | 20 | 46 | 114 | 585 |
| Comparative example 3 | 55 | 0.07 | 0.09 | 0.08 | 2 | 39 | 105 | 412 |

Example 3

A 150-mL glass reaction vessel equipped with a stirrer and a distillation tube was charged with 100.00 g (bisphenol C 0.39 mol) of the bisphenol C composition prepared in Example 1, 86.49 g (0.4 mol) of diphenyl carbonate, and 479 µL of 400 mass ppm aqueous cesium carbonate. The glass reaction vessel was evacuated to a pressure of approximately 100 Pa and was then filled with nitrogen to atmospheric pressure. This operation was repeated three times to replace the atmosphere in the reaction vessel with nitrogen. The reaction vessel was then immersed in an oil bath at 200° C. to dissolve the contents.

The rotational speed of the stirrer was set at 100 revolutions per minute. The absolute pressure in the reaction vessel was decreased from 101.3 kPa to 13.3 kPa over 40 minutes while phenol produced as a by-product by oligomerization of bisphenol C and diphenyl carbonate in the reaction vessel was distilled off. Transesterification was then performed for 80 minutes while the pressure in the reaction vessel was maintained at 13.3 kPa and while the phenol was further distilled off. The external temperature of the reaction vessel was then increased to 250° C., and the absolute pressure in the bisphenol C composition produced in Example 2 was used instead of 100.00 g (bisphenol C 0.39 mol) of the bisphenol C composition produced in Example 1.

The time from heating to 280° C. to the completion of polymerization (later stage polymerization time) was 220 minutes.

The polycarbonate resin had a viscosity-average molecular weight (Mv) of 24800 and a pellet YI of 6.5.

The trimethyl bisphenol A in the alkaline hydrolysate of the polycarbonate resin constituted 16200 mass ppm of the polycarbonate resin.

Comparative Example 3

Comparative Example 3 was performed in the same manner as in Example 3 except that 100.00 g (bisphenol C 0.39 mol) of the bisphenol C composition produced in Comparative Example 1 was used instead of 100.00 g (bisphenol C 0.39 mol) of the bisphenol C composition produced in Example 1.

The time from heating to 280° C. to the completion of polymerization (later stage polymerization time) was 230 minutes.

The polycarbonate resin had a viscosity-average molecular weight (Mv) of 24800 and a pellet YI of 10.2.

The trimethyl bisphenol A in the alkaline hydrolysate of the polycarbonate resin constituted 2 mass ppm of the polycarbonate resin.

Table 2 summarizes the trimethyl bisphenol A content of the alkaline hydrolysate of the polycarbonate resin with respect to the polycarbonate resin and the pellet YI of the polycarbonate resin in Examples 3 and 4 and Comparative Example 3.

Table 2 shows that the trimethyl bisphenol A component in the polycarbonate resin improves the pellet YI.

TABLE 2

| | Trimethyl bisphenol A content of alkaline hydrolysate of polycarbonate resin (based on polycarbonate resin: mass ppm) | Pellet YI of polycarbonate resin |
|---|---|---|
| Example 3 | 160 | 6.9 |
| Example 4 | 16200 | 6.5 |
| Comparative example 3 | 2 | 10.2 |

Although the present invention has been described in detail with reference to particular embodiments, it will be apparent to those skilled in the art that various modifications may be made therein without departing from the spirit and scope of the present invention.

The present application is based on Japanese Patent Application No. 2019-047450 filed on Mar. 14, 2019, Japanese Patent Application No. 2019-047453 filed on Mar. 14, 2019, Japanese Patent Application No. 2019-047454 filed on Mar. 14, 2019, Japanese Patent Application No. 2019-234571 filed on Dec. 25, 2019, and Japanese Patent Application No. 2019-234572 filed on Dec. 25, 2019, which are incorporated by reference in their entirety.

The invention claimed is:

1. A bisphenol composition, comprising:
   95% or more by mass of a first bisphenol, and
   150 mass ppm or more of a second bisphenol represented by formula (II),
   wherein the bisphenol composition has a methanol dissolution color (Hazen color number) of 1 or less,

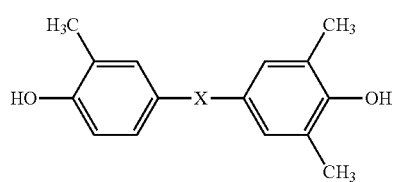

(II)

wherein:
X denotes a single bond, —CR$^{11}$R$^{12}$—, —O—, —CO—, —S—, —SO—, or —SO$_2$—,
R$^{11}$ and R$^{12}$ independently denote a hydrogen atom or an alkyl group having 1 to 10 carbon atoms, and R$^{11}$ and R$^{12}$ may be bonded to each other to form a ring.

2. The bisphenol composition according to claim 1, wherein the first bisphenol is a bisphenol represented by formula (I),

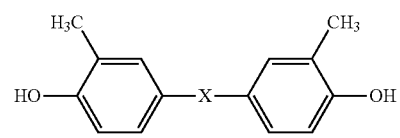

(I)

wherein:
X denotes a single bond, —CR$^{11}$R$^{12}$—, —O—, —CO—, —S—, —SO—, or —SO$_2$—,
R$^{11}$ and R$^{12}$ independently denote a hydrogen atom or an alkyl group having 1 to 10 carbon atoms, and R$^{11}$ and R$^{12}$ may be bonded to each other to form a ring.

3. The bisphenol composition according to claim 1, wherein the second bisphenol represented by formula (II) in the bisphenol composition constitutes 20,000 mass ppm or less of the bisphenol composition.

4. The bisphenol composition according to claim 1, wherein the second bisphenol represented by formula (II) is one or more selected from the group consisting of 2-(4-hydroxy-3-methylphenyl)-2-(4-hydroxy-3,5-dimethylphenyl) propane, 1-(4-hydroxy-3-methylphenyl)-1-(4-hydroxy-3,5-dimethylphenyl) cyclohexane, and 1-(4-hydroxy-3-methylphenyl)-1-(4-hydroxy-3,5-dimethylphenyl)-3,3,5-trimethylcyclohexane.

5. The bisphenol composition according to claim 1, wherein the bisphenol composition melted at 190° C. for 30 minutes has a Hazen color number of 100 or less measured with "SE6000" manufactured by Nippon Denshoku Industries Co., Ltd.

6. The bisphenol composition according to claim 1, wherein the bisphenol composition has a sodium content of less than 0.5 mass ppm.

7. The bisphenol composition according to claim 1, wherein the bisphenol composition has an iron content of 0.5 mass ppm or less.

8. The bisphenol composition according to claim 1, wherein the bisphenol composition has an aluminum content of 0.1 mass ppm or less.

9. The bisphenol composition according to claim 2, wherein the first bisphenol represented by the general formula (I) is one or more selected from the group consisting of 2,2-bis(4-hydroxy-3-methylphenyl) propane, 1,1-bis(4-hydroxy-3-methylphenyl) cyclohexane, and 1,1-bis(4-hydroxy-3-methylphenyl)-3,3,5-trimethylcyclohexane.

10. A method for producing the bisphenol composition according to claim 1, the method comprising:
   obtaining the second bisphenol represented by formula (II) as a by-product when the first bisphenol is produced.

11. A method for producing a polycarbonate resin, the method comprising:
   introducing the bisphenol composition according to claim 1 when the polycarbonate resin is prepared.

12. A polycarbonate resin, comprising:
   at least a repeating structural unit represented by formula (A):

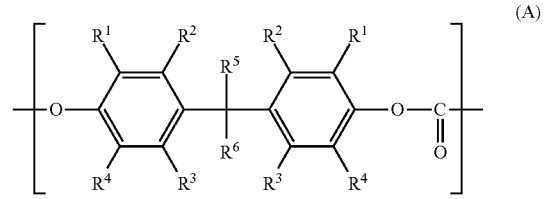

(A)

wherein $R^1$ to $R^6$ independently denote a hydrogen atom, a halogen atom, an alkyl group, an alkoxy group, or an aryl group, and the alkyl group, the alkoxy group, and the aryl group may be substituted or unsubstituted, $R^5$ and $R^6$ may be bonded or cross-linked between the two groups, and $R^5$, $R^6$, and an adjacent carbon atom may be bonded together and form a cycloalkylidene group optionally containing a heteroatom, wherein a compound produced by alkaline hydrolysis of the polycarbonate resin contains a first bisphenol represented by formula (I); and a second bisphenol represented by formula (II), which constitutes 160 mass ppm or more of the polycarbonate resin:

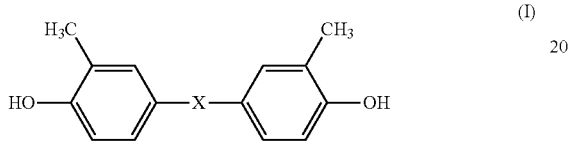
(I)

wherein X denotes a single bond, —$CR^{11}R^{12}$—, —O—, —CO—, —S—, —SO—, or —$SO_2$—, $R^{11}$ and $R^{12}$ independently denote a hydrogen atom or an alkyl group having 1 to 10 carbon atoms, and $R^{11}$ and $R^{12}$ may be bonded to each other to form a ring,

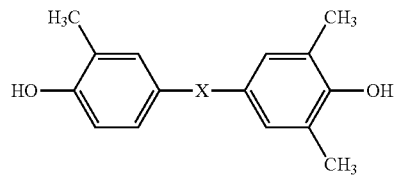
(II)

wherein X denotes a single bond, —$CR^{11}R^{12}$—, —O—, —CO—, —S—, —SO—, or —$SO_2$—, $R^{11}$ and $R^{12}$ independently denote a hydrogen atom or an alkyl group having 1 to 10 carbon atoms, and $R^{11}$ and $R^{12}$ may be bonded to each other to form a ring, and wherein a raw material for preparation of the polycarbonate resin is a bisphenol composition comprising the bisphenol represented by formula (I) and the bisphenol represented by formula (II), and the bisphenol coposition has a methanol dissolution color (Hazen color number) of 1 or less.

13. The polycarbonate resin according to claim 12, wherein the second bisphenol represented by formula (II) constitutes 20,000 mass ppm or less of the polycarbonate resin.

14. The polycarbonate resin according to claim 12, wherein the polycarbonate resin has a viscosity-average molecular weight of 15,000 or more and 35,000 or less.

15. The polycarbonate resin according to claim 12, wherein the polycarbonate resin has a pellet YI of 10 or less.

* * * * *